(12) United States Patent
Hubschwerlen et al.

(10) Patent No.: US 7,820,823 B2
(45) Date of Patent: Oct. 26, 2010

(54) DUAL ACTION ANTIBIOTICS

(75) Inventors: Christian Hubschwerlen, Durmenach (FR); Jean-Luc Specklin, Kembs-Schaferhof (FR)

(73) Assignee: Morphochem Aktiengesellschaft Fur Kominatorische Chemi, Munich (DE)

( * ) Notice: Subject to any disclaimer, the term of this patent is extended or adjusted under 35 U.S.C. 154(b) by 1478 days.

(21) Appl. No.: 10/491,519

(22) PCT Filed: Oct. 4, 2002

(86) PCT No.: PCT/EP02/11163

§ 371 (c)(1),
(2), (4) Date: Dec. 17, 2004

(87) PCT Pub. No.: WO03/032962

PCT Pub. Date: Apr. 24, 2003

(65) Prior Publication Data

US 2005/0096343 A1    May 5, 2005

Related U.S. Application Data

(60) Provisional application No. 60/327,162, filed on Oct. 4, 2001.

(51) Int. Cl.
C07D 215/00 (2006.01)
A61K 43/42 (2006.01)
(52) U.S. Cl. ........................ 546/153; 546/156; 514/311; 514/312
(58) Field of Classification Search ................ 546/156, 546/153; 514/314, 312
See application file for complete search history.

(56) References Cited

U.S. PATENT DOCUMENTS

| | | | |
|---|---|---|---|
| 4,840,956 A | 6/1989 | Domagala et al. ........... 514/312 |
| 5,221,676 A | 6/1993 | Laborde et al. ............. 514/300 |
| 5,491,139 A | 2/1996 | White et al. | |
| 2004/0132764 A1 | 7/2004 | Locher et al. | |
| 2007/0004769 A1 | 1/2007 | Hubschwerlen et al. | |
| 2007/0155714 A1 | 7/2007 | Hubschwerlen et al. | |
| 2008/0027040 A1 | 1/2008 | Hubschwerlen et al. | |

FOREIGN PATENT DOCUMENTS

| CA | 2424402 | 8/2002 |
|---|---|---|
| CA | 2450982 | 1/2003 |
| CN | 1520412 | 8/2004 |
| DE | 19601265 | 7/1997 |
| EP | 0266576 | 5/1988 |
| EP | 0390215 | 10/1990 |
| ES | 0101559 | 6/2001 |
| JP | 02069478 | 3/1990 |
| JP | 2004518677 | 6/2004 |
| JP | 2004521147 | 7/2004 |
| KR | 10 2000 0067306 | 11/2000 |
| KR | 2004-30712 | 1/2005 |
| WO | 93/09103 | 5/1993 |
| WO | WO 93/09103 | 5/1993 |
| WO | WO 97/30995 | 8/1997 |
| WO | WO 99/28317 | 6/1999 |
| WO | 01/46164 | 6/2001 |
| WO | 02059116 | 8/2002 |
| WO | WO 02/059116 A2 | 8/2002 |
| WO | 03002560 | 1/2003 |
| WO | 2004096221 | 11/2004 |
| WO | 2005/023801 | 3/2005 |
| WO | 2005/058888 | 6/2005 |

OTHER PUBLICATIONS

Wolff, Manfred E. "Burger's Medicinal Chemistry, 5ed, Part I", John Wiley & Sons; 1995, pp. 975-977.*
Banker (Modern Pharmaceutics) Banker, G.S. et al, "Modern Pharmaceutics, 3ed.", Marcel Dekker, New York, 1996, pp. 451 and 596.*
McGraw-Hill Dictionary of Chemical Terms(1990), pp. 282.*
Concise Encyclopedia Chemistry (1993).*
Hawlev's Condensed Chemical Dictionary (1993), 594.*
International Search Report for International Application No. PCT/EP02/11163 dated Apr. 4, 2003.
Hubschwerlen, Christian et al., Design, synthesis and biological evaluation of oxazolidinone-quinolone hybrids, Bioorganic & Medicinal Chemistry 2003, 11 pp. 2313-2319.
Hubschwerlen, Christian et al., Structure-activity relationship in the oxazolidinone-quinolone hybrid series: influence of the central spacer on the antibacterial activity and the mode of action, Bioorganic & Medicinal Chemistry 2003, 13 pp. 4229-4233.
Locher, et al. 42nd ICAAC (2002), poster and abstract F-1317, (ICAAC 2002: San Diego, CA Sep. 27-30, 2002).
Hubschwerlen, Christian et al., 43rd ICAAC, 2003 Chicago, IL Sep. 14-17, Abstract F-2144.
International Search Report issued on Feb. 5, 2003 in related application No. PCT/EP02/10765.
International Search Report issued on Jan. 28, 2003 in related application No. PCT/EP02/10766.

* cited by examiner

*Primary Examiner*—Janet L. Andres
*Assistant Examiner*—Raymond Covington
(74) *Attorney, Agent, or Firm*—Sonnenschien Nath & Rosenthal LLP

(57) ABSTRACT

The present invention relates to compounds of the Formula (I) that are useful antimicrobial agents and effective against a variety of multi-drug resistant bacteria.

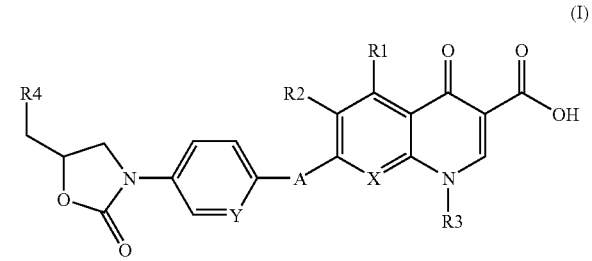

26 Claims, No Drawings

DUAL ACTION ANTIBIOTICS

The present invention describes new compounds in which the pharmacophores of quinolone and oxazolidinone are chemically linked together through a linker that is stable under physiological conditions and a pharmaceutical antibacterial composition containing these compounds. These dual action compounds are useful antimicrobial agents effective against a variety of human and veterinary pathogens including Gram positive aerobic bacteria such as multiply-resistant staphylococci, streptococci and enterococci as well as Gram negative bacteria such as *Moraxella catarrhalis* and *Haemophilus influenza* and anaerobic organisms such as *bacteroides* spp. and *Clostridia* spp. species and acid-fast organism such as *Mycobacterium tuberculosis, Mycobacterium avium* spp.

The intensive use of antibiotics has exerted a selective evolutionary pressure on microorganisms to produce genetically based resistance mechanisms. Modern medicine and socioeconomic behavior exacerbates the problem of resistance development by creating slow growth situations for pathogenic microbes, e.g. artificial joints-related infections, and by supporting long-term host reservoirs, e.g. in immunocompromised patients.

In hospital settings, an increasing number of strains of *Staphylococcus aureus, Streptococcus pneumoniae, Enterococcus* sp., and *Pseudomonas aeruginosa*, major sources of infections, are becoming multi-drug resistant and therefore difficult if not impossible to treat:

*S. aureus* is β-lactam, quinolone and now even vancomycin resistant.

*S. pneumoniae* is becoming resistant to penicillin and even to new macrolides.

*Enteroccocci* are quinolone and vancomycin resistant and β-lactams were never efficacious against these strains. The only alternative is to use oxazolidinones but these compounds are not bactericidal and the safety margin is rather low. Further, even with these drugs, resistance already appears in clinical practice.

In addition, microorganisms that are causing persistent infections are increasingly being recognized as causative agents or cofactors of severe chronic diseases like peptic ulcers or heart diseases.

The present invention provides new compounds of Formula (I) that are useful antimicrobial agents and effective against a variety of multi-drug resistant bacteria:

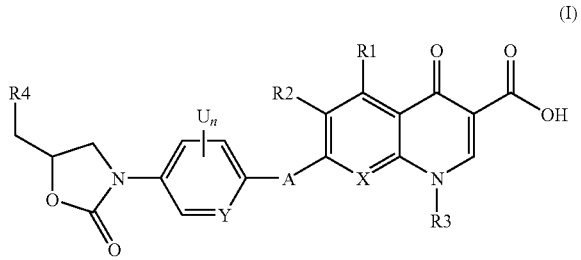

(I)

wherein

A is a direct bond, a NH, O, S, SO, $SO_2$, $SO_2NH$, $PO_4$, —NH—CO—NH—, —CO—NH—, —CO—, —CO—O—, —NH—CO—O—, an alkylen group, an alkenylen group, an alkinylen group, a heteroalkylen group, an arylen group, a heteroarylen group, a cycloalkylen group, a heterocycloalkylen group, an alkylarylen group or a heteroarylalkylen group or a combination of two or more of these atoms or groups;

X is CR5 or N;
Y is CR6 or N;
U is F or Cl;
n is 0, 1, 2 or 3;
R1 is H, F, Cl, Br, I, OH, $NH_2$, an alkyl group or a heteroalkyl group;
R2 is H, F or Cl;
R3 is H, an alkyl group, an alkenyl group, an alkinyl group, a heteroalkyl group, a cycloalkyl group, a heterocycloalkyl group, an aryl group, a heteroaryl group, an alkylaryl group or a heteroarylalkyl group; all of which may be substituted with one, two or more halogen atoms like F or Cl.
R4 is a heteroalkyl group, a cycloalkyl group, a heterocycloalkyl group, an aryl group, a heteroaryl group, an alkylaryl group or a heteroarylalkyl group;
R5 is H, F, Cl, OH, $NH_2$, an alkyl group or a heteroalkyl group, or
R3 and R5 can be linked via an alkylen, an alkenylen or a heteroalkylen group or be a part of a cycloalkylen or heterocyclo-alkylen group; in case R3 is no H and R5 is no H, F, OH, $NH_2$ or Cl;
R6 is H, F, Cl or OMe;
or a pharmacologically acceptable salt, solvate, hydrate or formulation thereof.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

The term alkyl refers to a saturated or unsaturated (i.e. alkenyl and alkinyl) straight or branched chain alkyl group, containing from one to ten, preferably one to six carbon atoms for example methyl, ethyl, propyl, iso-propyl, butyl, iso-butyl, sec-butyl, tert-butyl, n-pentyl, iso-pentyl n-hexyl, 2,2-dimethylbutyl, n-octyl; ethenyl(vinyl), propenyl(allyl), iso-propenyl, n-pentyl, butenyl, isoprenyl or hexa-2-enyl; ethinyl, propinyl or butinyl groups. Any alkyl group as defined herein may be substituted with one, two or more substituents, for example F, Cl, Br, I, $NH_2$, OH, SH or $NO_2$.

The terms alkenyl and alkinyl refer to a unsaturated straight or branched chain alkyl group (having one, two or more double and/or triple bonds, an alkenyl preferably having one or two double bonds and an alkinyl preferably having one or two triple bonds), containing from one to ten, preferably one to six carbon atoms for example: ethenyl(vinyl), propenyl (allyl), iso-propenyl, n-pentenyl, butenyl, isoprenyl or hexa-2-enyl; ethinyl, propinyl or butinyl groups. Any alkenyl or alkinyl group as defined herein may be substituted with one, two or more substituents, for example F, Cl, Br, I, $NH_2$, OH, SH or $NO_2$.

The term heteroalkyl refers to an alkyl group as defined herein where one or more carbon atoms are replaced by an oxygen, nitrogen, phosphorous or sulphur atom for example an alkoxy group such as methoxy, ethoxy, propoxy, iso-propoxy, butoxy or tert.-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, $NH_2$, OH, SH or $NO_2$.

The term cycloalkyl refers to a saturated or partially unsaturated (having one, two or more double and/or triple bonds), cyclic group with one, two or more rings, having three to 14 carbon ring-atoms, preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heterocycloalkyl refers to a cycloalkyl group as defined herein where one, two or more carbon ring-atoms are replaced by one, two or more oxygen, nitrogen, phosphorous or sulphur atoms or $S(0)_{1-2}$ groups for example piperidino, morpholino or piperazino groups.

The term aryl refers to an aromatic cyclic group with one, two or more rings, having five to 14 carbon ring-atoms preferably from five or six to ten carbon ring-atoms, for example phenyl or naphthyl groups. Any aryl group as defined herein may be substituted with one, two or more substituents, for example F, Cl, Br, I, OH, $NH_2$, SH, $N_3$, $NO_2$, alkyl groups such as methyl or ethyl, heteroalkyl groups such as methoxy, methylamino, dimethylamino or cyanide.

The term heteroaryl refers to an aryl group as defined herein where one, two or more ring-carbon atoms are replaced by an oxygen, nitrogen, boron, phosphorous or sulphur atom, for example pyridyl, imidazolyl, pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups.

The terms arylalkyl, alkylaryl and heteroarylalkyl, heteroalkylaryl refer to groups that comprise both aryl or, respectively, heteroaryl as well as alkyl and/or heteroalkyl and/or cycloalkyl and/or heterocycloalkyl groups.

Preferred and/or advantageous embodiments of the invention are subject-matter of the subclaims.

Preferred are compounds of Formula (I), wherein R1 is H or $NH_2$.

Further preferred are compounds of Formula (I), wherein R2 is H or F.

Moreover preferred are compounds of Formula (I), wherein R3 is an ethyl, a 2-propyl, a C3-C6 cycloalkyl, a phenyl or a pyridyl group. All these groups may be substituted by one, two or more fluorine atoms or amino groups.

Moreover preferred are compounds of Formula (I), wherein R3 is a cyclopropyl group.

Further preferred are compounds of Formula (I), wherein R3 and R5 together form a bridge of the formula —O—$CH_2$—N(Me)- or —O—$CH_2$—CH(Me)-. Herein, the preferred stereochemistry at the chiral center is the one giving the S configuration in the final compound.

Further preferred are compounds of Formula (I), wherein R4 is a group of the formula —NHCOCH=CHAryl, —OHeteroaryl (especially -oxa-3-oxazol), —$NHSO_2Me$, —NHCOOMe, $NHCS_2Me$, $NHCSNH_2$, —NHCSOMe or —NHCOMe.

Especially preferred are compounds of Formula (I), wherein R4 is an acetylamino group.

Moreover preferred are compounds of Formula (I), wherein R5 is H, F, Cl or a methoxy group which may be substituted by one, two or three fluorine atoms.

Further preferred are compounds of formula (I), wherein X is N or CH.

Further preferred are compounds of Formula (I), wherein Y is N or CF.

Further preferred are compounds of Formula (I), wherein n is 0.

Further preferred are compounds of Formula (I), wherein A is a bond.

Further preferred are compounds of Formula (I), wherein A is a group of the formula

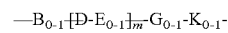

wherein the group B is an alkylene, which may be substituted by one, two or more fluorine atoms, a —NH— group, or a heteroalkylen group, which may be substituted by one, two or more fluorine atoms and/or at the optionally present nitrogen atoms by an alkyl or an acyl group;

the groups D independently of each other are optionally anellated heterocycloalkylen groups with 1, 2, 3 or 4 nitrogen atoms, which heterocycloalkylen groups may each be substituted by one, two or more fluorine atoms and/or which each may be substituted at one, two, three or four nitrogen atoms by an alkyl or an acyl group;

the groups E independently of each other are an alkylene, which may be substituted by one, two or more fluorine atoms, a —NH— group, or a heteroalkylen group, which may be substituted by one, two or more fluorine atoms and/or at the optionally present nitrogen atoms by an alkyl or an acyl group;

the groups G independently of each other are optionally anellated heterocycloalkylen groups with 1, 2, 3 or 4 nitrogen atoms, which heterocycloalkylen groups may each be substituted by one, two or more fluorine atoms and/or which each may be substituted at one, two, three or four nitrogen atoms by an alkyl or an acyl group;

the group K is an alkylene, which may be substituted by one, two or more fluorine atoms, a —NH— group, or a heteroalkylen group, which may be substituted by one, two or more fluorine atoms and/or at the optionally present nitrogen atoms by an alkyl or an acyl group; and m=1, 2, 3 or 4.

Moreover preferred are compounds of Formula (I), wherein A is a cycloalkylen or a alkylcycloalkylen group that contains 2, 3 or 4 nitrogen atoms and may be substituted by one, two or more fluorine atoms and the nitrogen atoms may be substituted by an alkyl or an acyl group.

Further preferred are compounds of Formula (I), wherein A is selected from the following groups which may be further substituted by one, two or more fluorine atoms or by an alkyl group which may be substituted by one, two or more fluorine atoms, and wherein the amino groups may be substituted by an alkyl or an acyl group:

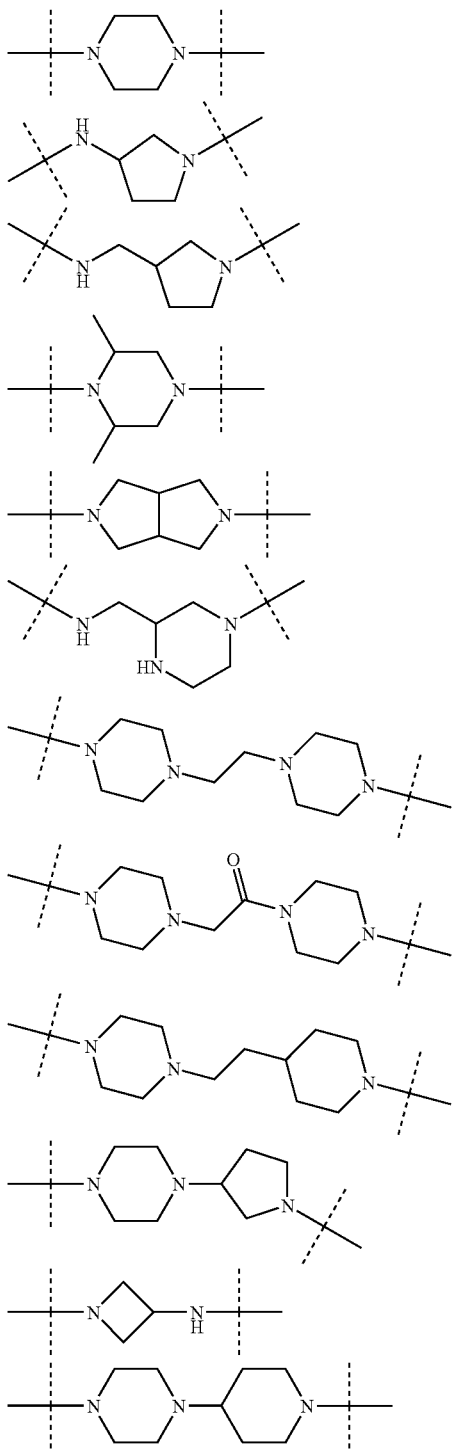

Further preferred are compounds of Formula (I), wherein the absolute configuration at C-5 of the oxazolidinone ring is (S) according to the Cahn-Ingold-Prelog nomenclature system.

Moreover preferred are the following compounds:

7-(4-{4-[5-(acetylamino-methyl)-2-oxo-oxazolidin-3-yl]-2-fluoro-phenyl}-piperazin-1-yl)-1-cyclopropyl-6-fluoro-4-oxo-1,4-dihydro-quinoline-3-carboxylic acid 9-(4-{4-[5-(acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3a-aza-phenalene-5-carboxylic acid 7-[(3R)-3-{4-[(5S)-5-(Acetylamino-methyl)-2-oxo-oxazolidin-3-yl]-2-fluoro-phenylamino}-pyrrolidin-1-yl]-1cyclopropyl-6-fluoro-4-oxo-1,4-dihydro-quinoline-1-carboxylic acid 7-(4-{4-[(5S)-5-(Acetylamino-methyl)-2-oxo-oxazolidin-3-yl]-2-fluoro-phenyl}-piperazin-1-yl)-6-fluoro-1-(5-fluoro-pyridin-2-yl)-4-oxo-1,4-dihydro-quinoline-3-carboxylic acid 7-(4-{(5S)-5-(Acetylamino-methyl)-2-oxo-oxazolidin-3-yl]-2-fluoro-phenyl}-piperazin-1-yl)-1-(2,4-difluoro-phenyl)-6-fluoro-4-oxo-1,4-dihydro-quinoline-3-carboxylic acid 7-(4-{4-[(5S)-5-(Acetylamino-methyl)-2-oxo-oxazolidin-3-yl]-2-fluoro-phenyl}-piperazin-1-yl)-1-cyclopropyl-8-methoxy-4-oxo-1,4-dihydro-quinoline-3-carboxylic acid 9-(4-{4-[(5S)-5-(Acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic acid 7-(4-{[(5S)-5-(Acetylamino-methyl)-2-oxo-oxazolidin-3-yl]-2-fluoro-phenyl}-piperazin-1-yl)-1-cyclopropyl-6-fluoro-4-oxo-1,4-dihydro-[1,8]naphthyridine-3-carboxylic acid 7-{4-[2-(4-{4-[5-(Acetylamino-methyl)-2-oxo-oxazolidin-3-yl]-2-fluoro-phenyl}-piperazin-1-yl)-ethyl]-piperazin-1-yl}-1-cyclopropyl-6-fluoro-4-oxo-1,4-dihydro-quinoline-3-carboxylic acid 7-{4-[2-(4-{4-[5-(Acetylamino-methyl)-2-oxo-oxazolidin-3-yl]-2-fluoro-phenyl}-piperazin-1-yl)-ethyl]-piperazin-1-yl}-1-cyclopropyl-6-fluoro-4-oxo-1,4-dihydro-quinoline-3-carboxylic acid 7-{4-[2-(4-{4-[(5S)-5-(Acetylamino-methyl)-2-oxo-oxazolidin-3-yl]-2-fluoro-phenyl}-piperazin-1-yl)-2-oxo-ethyl]-piperazin-1-yl}-1-cyclopropyl-6-fluoro-4-oxo-1,4-dihydro-quinolone-3-carboxylic acid 7-(3-{4-[5(S)-5-(Acetylamino-methyl)-2-oxo-oxazolidin-3-yl]-2-fluoro-phenylamino}-azetidin-1-yl)-1-cyclopropyl-6-fluoro-4-oxo-1,4-dihydro-[1,8]naphthyridine-3-carboxylic acid 7-[(3R)-3-{4-[(5S)-5-(Acetylamino-methyl)-2-oxo-oxazolidin-3-yl]-2-fluoro-phenylamino}-pyrrolidin-1-yl]-1-cyclopropyl-6-fluoro-4-oxo-1,4-dihydro-[1,8]-naphthyridine-3-carboxylic acid 7-[(3R)-3-(4-{4[(5S)-5-(Acetylamino-methyl)-2-oxo-oxazolidin-3-yl]-2-fluoro-phenyl}-piperazin-1-yl)-pyrrolidin-1-yl]-1-cyclopropyl-6-fluoro-4-oxo-1,4-dihydro-[1,8]naphthyridine-3-carboxylic acid 1-Cyclopropyl-6-fluoro-7-(4-{2-fluoro-4-[(5S)-5-(methoxythiocarbonylamino-methyl)-2-oxo-oxazolidin-3-yl]-phenyl}-piperazin-1-yl)-4-oxo-1,4-dihydro-[1,8]-naphthyridine-3-carboxylic acid 1-Cyclopropyl-6-fluoro-7-(4-{2-fluoro-4-[(5S)-5-(methylsulfanylthiocarbonylamino-methyl)-2-oxo-oxazolidin-3-yl]-phenyl}-piperazin-1-yl)-4-oxo-1,4dihydro-[1,8]naphthyridine-3-carboxylic acid 1-Cyclopropyl-6-fluoro-{4-[2-fluoro-4-{(5S)-2-oxo-5-thioureidomethyl-oxazolidin-3-yl]-phenyl]-piperazin-1-yl}-4-oxo-1,4-dihydro-[1,8]naphthyridine-3-carboxylic acid The present invention also relates to pharmacologically acceptable salts, or solvates and hydrates, respectively, and to compositions and formulations of compounds of Formula (I). The present invention describes procedures to produce pharmaceutically useful agents, which contain these compounds, as well as the use of these compounds for the production of pharmaceutically useful agents.

The pharmaceutical compositions according to the present invention contain at least one compound of Formula I as the active agent and optionally carriers and/or diluents and/or adjuvants. Optionally the pharmaceutical compositions according to the present invention may also contain additional known antibiotics.

Examples of pharmacologically acceptable salts of sufficiently basic compounds of Formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of Formula (I) may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts. Compounds of Formula (I) may be solvated, especially hydrated. The hydratisation can occur during the process of production or as a consequence of the hygroscopic nature of the initially water free compounds of Formula (I). The compounds of Formula (I) contain asymmetric C-atoms and may be present either as achiral compounds, mixtures of diastereomers, mixtures of enantiomers or as optically pure compounds.

The present invention also relates to pro-drugs which are composed of a compound of Formula (I) and at least one pharmacologically acceptable protective group which will be cleaved off under physiological conditions, such as an alkoxy-, aralkyloxy-, acyl-, acyloxymethyl group (e.g. pivaloyloxymethyl), an 2-alkyl-, 2-aryl- or 2-aralkyl-oxycarbonyl-2-alkylidene ethyl group or an acyloxy group as defined herein, e.g. ethoxy, benzyloxy, acetyl or acetyloxy.

As mentioned above, therapeutically useful agents that contain compounds of Formula (I), their solvates, salts or formulations are also comprised in the scope of the present invention. In general, compounds of Formula (I) will be administered by using the known and acceptable modes known in the art, either alone or in combination with any other therapeutic agent. Such therapeutically useful agents can be administered by one of the following routes: oral, e g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

A daily dosage per patient of about 1 mg to about 4000 mg especially about 50 mg to 3 g is usual with those of ordinary skill in the art appreciating that the dosage will depend also upon the age, conditions of the mammals, and the kind of diseases being treated or prevented. The daily dosage can be administered in a single dose or can be divided over several doses. An average single dose of about 50 mg, 100 mg, 250 mg, 500 mg, 1000 mg and 2000 mg can be contemplated.

The compounds of Formula (I) can for example be obtained by reacting an oxazolidinone bearing a group A as defined above that contains an amine with a 7-chloro or 7-fluoro quinolone derivative. To facilitate the reaction the quinolone reactant may be activated prior to its use by forming a complex with a Lewis acid like $BF_3$-etherate or any boron containing complex like boron acetate. The reaction is performed in a polar solvent like acetonitrile, 1-methyl-2-pyrrolidone, water, DMSO in presence of an organic base like triethylamine, N,N'dimethyl-p-toluidine, N-methylmorpholine, DBU, DABCO between 20 and 200° C. preferably between 80 and 130° C. The reaction can be performed under microwave activation

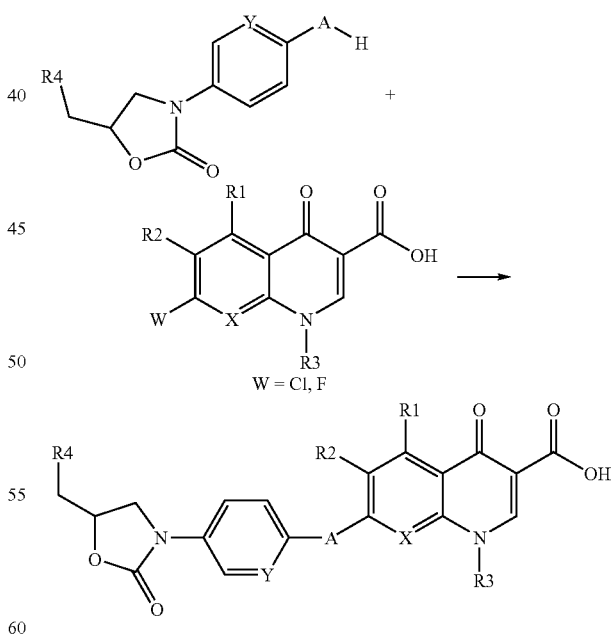

Alternatively, the product can be prepared from the corresponding 7-chloro-quinolone by substitution with a 4-nitrophenyl derivative bearing a group containing an amine and subsequent construction of the oxazolidinone through reduction of the nitro group, reaction with benzyl chloroformate, deprotonation with n-BuLi and reaction with a glycitol ester.

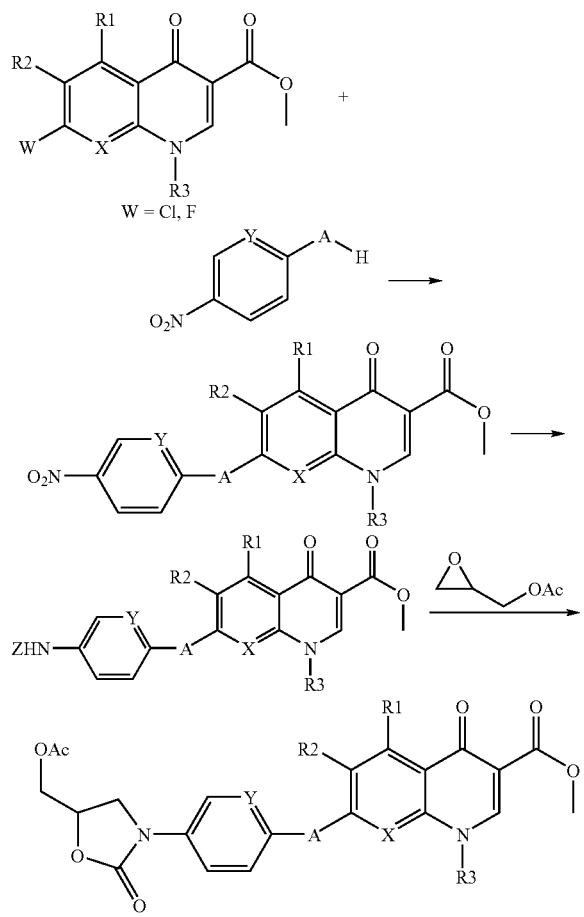

In the following the invention is described in more detail with reference to examples. These examples are intended for illustration only and are not to be construed as any limitation.

EXAMPLES

Example 1

7-(4-{4-[5-(acetylamino-methyl)-2-oxo-oxazolidin-3-yl]-2-fluoro-phenyl}-piperazin-1-yl)-1-cyclopropyl-6-fluoro-4-oxo-1,4-dihydro-quinoline-3-carboxylic Acid

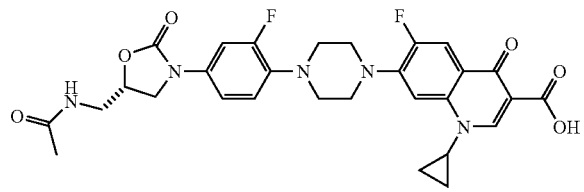

A mixture of 7-chloro-1-cyclopropyl-6-fluoro-4-oxo-1,4-dihydro-quinoline-3-carboxylate boron diacetate (described in WO8807998; 103 mg, 0.25 mmol), N-[3-(3-fluoro-4-piperazin-1-yl-phenyl)-2-oxo-oxazolidinon-5-ylmethyl]acetamide (described in J. Med Chem 1996, 39, 673-679 and U.S. Pat. No. 5,547,950; 100 mg, 0.3 mmol) and N,N'dimethyl-p-toluidine (0.054 ml, 0.375 mmol) were stirred at 120° C. in 0.5 ml of 1-methyl-2-pyrrolidone for 12 hours. The reaction mixture was poured into water and the resulting crystals were collected by filtration and purified by chromatography over silica gel. The interesting fractions were pooled affording 38 mg (26%) of beige material.

$C_{29}H_{29}F_2N_5O_6$ (581.5812)

mp 315-320° C. (dec)

MS: 582.4 (M+H); 580.4 (M−H).

Example 2

9-(4-{4-[5-(acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3a-aza-phenalene-5-carboxylic Acid

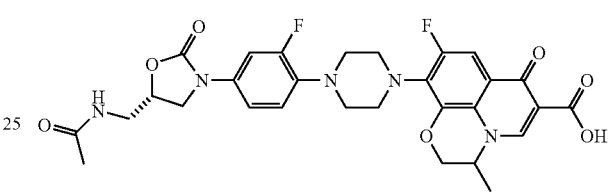

A suspension of 9,10-difluoro-2,3-dihydro-3-methyl-7-oxo-7H-pyrido-[1,2,3-de]-1,4-benzoxazine-6-carboxylic acid (commercially available from Aldrich (47267-0) and described in Chem. Pharm. Bull. 1987, 35, 1896-1902, 84 mg; 0.3 mmol), N-[3-(3-fluoro-4-piperazin-1-yl-phenyl)-2-oxo-oxazolidinon-5-ylmethyl]acetamide (described in J. Med Chem 1996, 39, 673-9 and U.S. Pat. No. 5,547,950; 121 mg, 0.36 mmol) and DABCO (43.7 mg, 0.39 mmol) in acetonitrile/water (7 ml, 2:1) was refluxed for 12 days. The acetonitrile was removed under reduced pressure and the residue was poured into water. The crystals were collected by filtration and further stirred in methanol (5 ml). The resulting crystals were recrystallised from DMF/water (4:1) affording 95 mg of beige material (53%).

$C_{29}H_{29}F_2N_5O_7$ (597.5806)

mp 258° C. (dec)

MS: 596.8 (M−H); 598.5 (M+H)

Example 3

7-((3R,S)-3-{4-[(5S)-5-(acetylamino-methyl)-2-oxo-oxazolidin-3-yl]-2-fluoro-phenylcarbamoyl}-piperazin-1-yl)-1-cyclopropyl-6-fluoro-4-oxo-1,4-dihydro-quinoline-3-carboxylic Acid

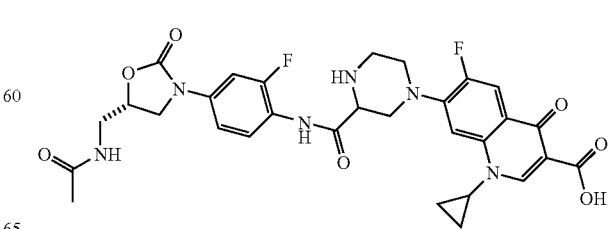

2 ([(5S)-5-(acetylaminomethyl)-2-oxo-oxazolidin-3-yl]-2-fluoro-phenylcarbamoyl)-piperazine-1,4-dicarboxylic Acid Di-Tert-Butyl Ester 0.210 ml of phosphoroxychloride was added at −15° C. to a solution of 0.4 g N[(5S)-3-(4-amino-3-fluoro-phenyl)-2-oxo-oxazolidin-5-ylmethyl]acetamide (1.5 mmol) and 0.545 g piperazine-1,2,4-tricarboxylic acid 1-4-di-tert-butyl ester (1.65 mmol) in 10 ml pyridine. The reaction was monitored by TLC. The reaction mixture was poured on ice, diluted with dichloromethane, the org. layer washed with water and brine, dried over Mg sulfate, filtered and evaporated. The residue was purified by chromatography, using a dichloromethane/methanol 95/5 as eluent leaving a colorless foam.

Yield: 0.390 g. 45%, C27H38FN5O8 (579.63), MS: 580.5 (M+H)+, 578.8 (M−H)− Method ESI+, ESI−.

(2R,S)-2([[(5S)-5-(Acetylaminomethyl)-2-oxo-oxazolidin-3-yl]-2-fluoro-phenylcarbamoyl)-piperazine A solution of 0.376 g 2([(5S)-5-(acetylaminomethyl)-2-oxo-oxazolidin-3-yl]-2-fluoro-phenylcarbamoyl)-piperazine-1,4-dicarboxylic acid di-tert-butyl ester in 10 ml of dichloromethane was diluted with 10 ml of 1.25 N HCl in methanol. The reaction was monitored by TLC. The solvents were evaporated, the residue dissolved in 10 ml water, neutralized with sodium bicarbonate, and the water layer evaporated to dryness. The residue was digested in a 1/1 dichloromethane/methanol solution, the insoluble salts filtered, and the filtrate evaporated. The residue was digested in ethyl acetate and the solid filtered.

Yield: 0.250 g, quant. C17H22FN5O4 (379.39), MS: 380.5 (M+H)+, method: ESI+.

7-((3R,S)-3-{4-[(5S)-5-(acetylamino-methyl)-2-oxo-oxazolidin-3-yl]-2-fluoro-phenylcarbamoyl}-piperazin-1-yl)-1-cyclopropyl-6-fluoro-4-oxo-1,4-dihydro-quinoline-3-carboxylic Acid A mixture of 175 mg 2([5-(acetylaminomethyl)-2-oxo-oxazolidin-3-yl]-2-fluoro-phenylcarbamoyl)-piperazine (0.46 mmol), 188 mg 7-chloro-6-fluoro-1-cyclopropyl-4-oxo-1,4-dihydroquinoline-3-carboxylatoboron diacetate and 154 mg of 1,4-diazabicyclo[2.2.2]octane (1.38 mmol) in 2 ml of N-methyl pyrrolidone was stirred at 100° C. under inert gas. The reaction was monitored by TLC. The mixture was poured in ether, the solid filtered and dried. The solid was purified by chromatography, using a dichloromethane/methanol 9/1 mixture with 1% acetic acid. The fractions with a rf of 0.1 were collected and evaporated.

Yield: 0.043 g, 18%. C30H30F2N6O7 (624.61), MS: 625.5 (M+H)+, 623.8 (M−H)−.

Known building blocks:
piperazine-1,2,4-tricarboxylic acid 1-4-di-tert-butyl ester: CAS 181955-79-3; Com. Source: Chem. Pacific Product List No 33681,
7-chloro-6-fluoro-1-cyclopropyl-4-oxo-1,4-dihydroquinoline-3-carboxylatoboron diacetate: Ger. Offen. (1996), DE 4428985.
(S)—N[3-(4-amino-3-fluoro-phenyl)-2-oxo-oxazolidin-5-ylmethyl]acetamide: Genin, Michael et al. Journal of Medicinal Chemistry (2000), 43(5), 953-970

Example 4

7-[(3R)-3-{4-[(5S)-5-(Acetylamino-methyl)-2-oxo-oxazolidin-3-yl]-2-fluoro-phenylamino}-pyrrolidin-1-yl]-1cyclopropyl-6-fluoro-4-oxo-1,4-dihydro-quinoline-1-carboxylic Acid

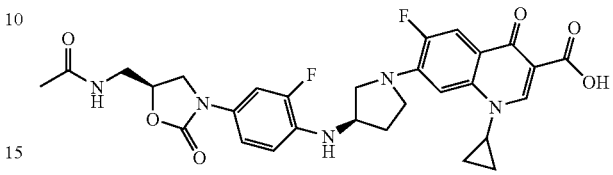

(3R)-3-(2-Fluoro-4-nitro-phenylamino)-pyrrolidine-1-carboxylic Acid Allyl Ester

A solution of 5.01 g of 3,4-difluoro nitrobenzene, 5.1 g (3R)-1-allyloxycarbonyl-3-amino pyrrolidine (30 mmol) and 6.27 ml of triethylamine (31.5 mmol) in 100 ml of ethyl acetate was stirred at reflux. The reaction was monitored by HPLC. The reaction was diluted with ethyl acetate, washed with water and brine, the org. layer dried over Mg sulfate, filtered and evaporated. The residue crystallized from an ether/hexane mixture.

Yield: 5.76 g, 59%. MW: 309.29 C14H16FN3O4

1H-NMR (δ ppm, 400 MHz, D6-DMSO): 1.09-2.24 (m, 2H, N—CH2-CH2-CH); 3.29-3.72 (m, 4H, CH2-N—CH2); 4.21-4.28 (m, 1H, N—CH); 4.52, (d, 2H, O—CH2); 5.15-5.32, (m, 2H, CH=CH2); 5.87-5.99, (m, 1H, CH=CH2); 6.94, (t, 1H, Ph-CH); 7.19, (d, 1H, NH); 7.9-7.99, (m, 2H, Ph-CH);

(3R)-3-(2-Fluoro-4-nitro-phenylamino)-pyrrolidine-1-carboxylic Acid Tert-Butyl Ester To a solution of 5.76 g (3R)-3-(2-fluoro-4-nitro-phenylamino)-pyrrolidine-1-carboxylic acid allyl ester (18.6 mmol) in 60 ml THF were added 130 mg of PdCl2{P(Ph)2} (0.186 mmol), 12.12 ml acetic acid (37.2 mmol), and 49.87 ml tributyl tinhydride (37.2 mmol). The reaction was stirred at rt for 1 hr. and monitored by TLC. A pale yellow solid precipitated. The suspension was diluted with 100 ml ether, the solid was filtered, washed with ether and hexane and dried. The solid was suspended in 10 ml THF, 4.87 g BOC anhydride (30 mmol) was added and the reaction stirred at rt. for 3 h and monitored by TLC. The reaction was diluted with ethyl acetate, the org layer washed with water and brine, dried over Mg sulfate, filtered and the filtrate evaporated. The residue was crystallized from an ether/hexane mixture.

Yield: 4.15 g, 68%. MW: 325.34 (C15H20FN3O4)

1H-NMR (400 MHz, D6-DMSO; δ ppm): 1.25, (s, 9H, t-but); 1.75-2.07 (m, 2H, N—CH2-CH2-CH); 3.07-3.5 (m, 4H, CH2-N—CH2); 4.05-4.1 (m, 1H, N—CH); 6.77-6.83, (t, 1H, Ph-CH); 7.01, (d, 1H, NH); 7.77-7.858, (m, 2H, Ph-CH);

(3R)-3-[Benzyloxycarbonyl-(4-benzyloxycarbonylamino-2-fluoro-phenyl)-amino]-pyrrolidine-1-carboxylic Acid Tert-Butyl Ester To a solution of 4 g of (3R)-3-(2-fluoro-4-nitro-phenylamino)-pyrrolidine-1-carboxylic acid tert-butyl ester (12.29 mmol) in 100 ml ethyl acetate and 50 ml methanol were added 1 g of Pd/C 10%. The suspension was stirred under hydrogen. The reaction was monitored by TLC. The catalyst was filtered, the filtrate evaporated to dryness, and the residue was dissolved in 100 ml of acetone. 25 ml of a saturated solution of sodium bicarbonate was added, than a 0° C. 3.63 ml of benzyl chloroformate (25.8 mmol). The reaction was stirred over night at rt and monitored by TLC. The acetone was evaporated, the water layer extracted twice with ethyl acetate, the org layer washed with water and brine, dried over Mg sulfate, filtered and the filtrate evaporated to dryness. The residue was purified by chromatography, using a 1/1 ethyl acetate/hexane mixture as eluent.

Yield: 6.03 g, 99%. MW: 563.63, C31H34FN3O6, MS: 562.4 (M−H)−, Method ESI−.

(3R)-3-{Benzyloxycarbonyl-[2-fluoro-4-{(5R)-5-hydroxymethyl-2-oxo-oxazolidin-3-yl}-phenyl]-amino}-pyrrolidine-1-carboxylic Acid Tert-Butyl Ester To a solution of 6.02 g (3R)-3-[benzyloxycarbonyl-(4-benzyloxycarbonylamino-2-fluoro-phenyl)-amino]-pyrrolidine-1-carboxylic acid tert-butyl ester (10.8 mmol) in 40 ml THF at −78° C. was added dropwise 7.62 ml of a 1.6 M N-butyl-lithium solution in N-hexane (12.2 mmol). The mixture was stirred at −78° C. for 10 min, than allowed to reach 0° C. 2.11 g of R(−)-glycidyl butyrate (14.6 mmol) was added. The reaction was allowed to reach 20° C. and was monitored by TLC. The reaction was diluted with ethyl acetate, washed with water and brine, dried over Mg sulfate, filtered and the filtrate evaporated. The residue was crystallized from an ethyl acetate/hexane mixture.

Yield: 3.36 g, 60%. MW: 529.47, (C27H32FN3O7) MS: 530.3 (M+H)+, Method ESI−.

(3R)-3-{[4-{(5R)-5-Azidomethyl-2-oxo-oxazolidin-3-yl}-2-fluoro-phenyl]-benzyloxycarbonyl-amino}-pyrrolidine-1-carboxylic Acid Tert-Butyl Ester To a solution 3.36 g of (3R)-3-{benzyloxycarbonyl-[2-fluoro-4-{(5R)-5-hydroxymethyl-2-oxo-oxazolidin-3-yl}-phenyl]-amino}-pyrrolidine-1-carboxylic acid tert-butyl ester (10.8 mmol) and 2.05 ml of triethylamine (10.8 mmol) in 40 ml of dichloromethane, was added at 0° C. 0.805 ml of methanesulfonyl chloride (10.8 mmol). The reaction was stirred at rt. and monitored by TLC. The reaction was diluted with water and washed with water and brine. The org. layer was dried over Mg sulfate, filtered and the filtrate evaporated The solid residue was dissolved in 10 ml of DMF and 1.38 g sodium azide (10.8 mmol) was added and the mixture stirred under inert gas at 80° C. for 20 hrs. The DMF was evaporated, the residue dissolved in ethyl acetate, washed with water and brine, dried over Mg sulfate, filtered and evaporated.

Yield: 4.07 g, 99%. MW: 554.58, (C27H31FN6O6) MS: 555.5 (M+H)+, Method ESI+.

(3R)3-{4-[(5S)-5-(Acetylaminomethyl)-2-oxo-oxazolidin-3-yl]-2-fluoro-phenylamino}-pyrrolidine-1-carboxylic Acid Tert-Butyl Ester To a stirred solution of 4.2 g of (3R)-3-{[4-{(5R)-5-azidomethyl-2-oxo-oxazolidin-3-yl}-2-fluoro-phenyl]-benzyloxycarbonyl-amino}-pyrrolidine-1-carboxylic acid tert-butyl ester (7.3 mmol) in 50 ml ethyl acetate were added 400 mg of Pd/C 10% and the mixture was stirred under hydrogen over night. The reaction was controlled by TLC. The Pd/C was filtered, the filtrate evaporated to dryness. The residue was dissolved in 5 ml acetic acid and 2 ml acetic anhydride was added. The reaction was stirred at rt for 2 hrs and monitored by TLC. The solvents were evaporated, the residue dissolved in ethyl acetate, washed with water and brine, dried over Mg sulfate, filtered and the filtrate evaporated to dryness.

Yield: 3.1 g, quantitative. MW: 436.48, (C21H29FN4O5) MS: 437.5 (M+H)+, Method ESI+.

N-{(5S)-3-[3-Fluoro-4-{(3R)-pyrrolidin-3-ylamino}-phenyl]-2-oxo-oxazolidin-5-ylmethyl}-acetamide A solution of 0.93 ml triethylsilane (7.3 mmol) (3R)3-{4-[(5S)-5-(acetylaminomethyl)-2-oxo-oxazolidin-3-yl]-2-fluoro-phenylamino}-pyrrolidine-1-carboxylic acid tert-butyl ester (7.3 mmol) in 40 ml of a CH2Cl2/TFA 1/1 mixture was stirred at rt and monitored by TLC. The solvents were evaporated, the residue dissolved in water and neutralized with a saturated sodium bicarbonate solution. The water was evaporated, the residue digested in a 1:1 CH2Cl2/MeOH solution, the solution treated with 500 mg of Fuller's earth, filtered and the filtrate evaporated.

Yield: 2.1 g, 85%. MW: 336.36, (C16H21FN4O3) MS: 337.6 (M+H)+, Method ESI+.

7-[(3R)-3-{4-[(5S)-5-(Acetylamino-methyl)-2-oxo-oxazolidin-3-yl]-2-fluoro-phenylamino}-pyrrolidin-1-yl]-1cyclopropyl-6-fluoro-4-oxo-1,4-dihydro-quinoline-1-carboxylic Acid A solution of 204 mg 7-chloro-6-fluoro-1-cyclopropyl-4-oxo-1,4-dihydroquinoline-3-carboxylatoboron diacetate (0.5 mmol), 252 mg N-{(5S)-3-[3-fluoro-4-{(3R)-pyrrolidin-3-ylamino}-phenyl]-2-oxo-oxazolidin-5-ylmethyl}-acetamide (0.75 mmol) and 112 mg DABCO (MW: 112.0, 1 mmol) in 5 ml DMSO was stirred for 50 h. The DMSO was evaporated. The residue was suspended in 10 ml ethanol with 100 μl triethylamine and stirred at room temperature for 20 hrs. The mixture was diluted with 20 ml water. The mixture was filtered and the solid collected. The solid was crystallized in a methanol/ethanol/dichloromethane mixture.

Yield: 16 mg, 3.6%. MW: 582.4, (C29H29F2N5O6) MS: 582.4 (M+H)+, Method ESI+.

Example 5

7-(4-{4-[(5S)-5-(Acetylamino-methyl)-2-oxo-oxazolidin-3-yl]-2-fluoro-phenyl}-piperazin-1-yl)-6-fluoro-1-(5-fluoro-pyridin-2-yl)-4-oxo-1,4-dihydro-quinoline-3-carboxylic Acid

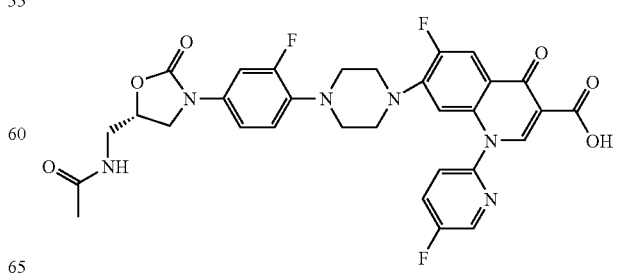

7-Chloro-6-fluoro-1-(5-fluoro-pyridin-2-yl)-4-oxo-1,4-dihydro-quinoline-3-carboxylic Acid Ethyl Ester A solution of 0.747 g of 2-(2,4-dichloro-5-fluoro-benzoyl)-3-ethoxy-acrylic acid ethyl ester (2.23 mmol) and 0.250 g of 2-amino-5-fluoropyridine (2.23 mmol) in 5 ml ethanol was stirred at reflux for 25 hrs. The reaction was monitored by TLC. The ethanol was evaporated and the last traces of ethanol were distilled from an azeotrope with a mixture of 10 ml heptane and 10 ml ethyl acetate. The yellow oil was dissolved in 10 ml of THF, reacted with 120 mg of a 50% NaH suspension in oil and stirred at reflux over night. The solvent was evaporated, the residue dissolved in dichloromethane/methanol 9:1, washed with water and brine, dried over Mg sulfate, filtered and evaporated. The residue was digested in ethyl acetate, and the solid filtered.

Yield: 583 mg, 72%. MW: 364.73, (C17H11ClF2N2O3) MS: 365.4 (M+H)$^+$, Method ESI$^+$.

7-chloro-6-fluoro-1-(5-fluoro-pyridin-2-yl)-4-oxo-1,4-dihydro-quinoline-3-carboxylic Acid A suspension of 0.5 g 7-chloro-6-fluoro-1-(5-fluoro-pyridin-2-yl)-4-oxo-1,4-dihydro-quinoline-3-carboxylic acid ethyl ester (1.37 mmol) in a mixture of 1.5 ml acetic acid and 1.5 ml 25% HCl was stirred at 90° C. over night. The reaction was monitored by HPLC. The suspension was poured into 50 ml water, the colorless crystals filtered and dried.

Yield: 461 mg, quant. MW: 336.68, (C15H7ClF2N2O3) MS: 337.5 (M+H)$^+$, Method ESI$^+$.

7-chloro-6-fluoro-1-(5-fluoro-pyridin-2-yl)-4-oxo-1,4-dihydro-quinoline-3-carboxylatoboron Diacetate To a stirred suspension of 380 mg 7-chloro-6-fluoro-1-(5-fluoro-pyridin-2-yl)-4-oxo-1,4-dihydro-quinoline-3-carboxylic acid (1.12 mmol) in 4 ml dichloromethane were added at 0° C. 0.31 ml triethylamine (d=0.726, 2.25 mmol) and 0.12 ml (d=1.1050, 1.68 mmol) acetyl chloride. The reaction mixture was allowed to warm up to RT, diluted with dichloromethane and washed twice with ice cold water and brine. The organic layer was dried over sodium sulfate, filtered and evaporated. The residue was crystallized from a dichloromethane/hexane mixture. 332 mg of the colorless crystals were suspended in 0.63 ml of acetic anhydride (MW: 102.9, d=1.08, 6.6 mmol), 78 mg anhydrous boric acid (MW: 61.83, 1.26 mmol) and 1 mg zinc chloride (MW: 136.28, 0.7 mmol) were added. The mixture was stirred at 80° C. for two hours. The reaction was poured on 10 g ice in 20 ml water and stirred. The colorless crystals were filtered, digested twice in 100 ml ethanol, filtered, washed with ether and hexane, and dried at RT under vacuum.

Yield: 226 mg, 43%. MW: 464.57, (C19H12BClF2N2O7)
1H-NMR (δ ppm; DMSO-D$_6$): 1.96 (s, 6H, acetate); 8.15 (d, 1H, pyridin), 8.25 (m, 2H, pyridin), 8.53 (d, 1H, quinoline); 8.87 (d, 1H, quinoline); 9.71 (s, 1H, allyl).

7-(4-{4-[(5S)-5-(Acetylamino-methyl)-2-oxo-oxazolidin-3-yl]-2-fluoro-phenyl}-piperazin-1-yl)-6-fluoro-1-(5-fluoro-pyridin-2-yl)-4-oxo-1,4-dihydro-quinoline-3-carboxylic Acid 212 mg of 7-chloro-6-fluoro-1-(5-fluoro-pyridin-2-yl)-4-oxo-1,4-dihydro-quinoline-3-carboxylatoboron diacetate (0.45 mmol), 306 mg N-{[(5S)-3-[3-fluoro-4-(1-piperazinyl)phenyl]-2-oxo-5-oxazolidinyl]methyl}-acetamide (0.9 mmol) and 2 ml DMSO were irradiated in a microwave oven for 7 periods of 2.30 min at 250 W in a closed reaction vessel under inert gas. The reaction was monitored by HPLC.

The DMSO was evaporated and the crude product was digested in 10 ml water and filtered. The residue was purified by chromatography using a CH$_2$Cl$_2$/MeOH 5% mixture.

Yield: 5 mg, 2%. MW: 636.59, (C31H27F3N6O6) MS: 637.2 (M+H)$^+$, Method ESI$^+$.

Known building blocks:
2-amino-5-fluoropyridine: 21717-96-4, aldrich 51868-9
2-(2,4-Dichloro-5-fluoro-benzoyl)-3-ethoxy-acrylic acid ethyl ester: 86483-52-5, WO0217916 A1

Example 6

7-(4-{(5S)-5-(Acetylamino-methyl)-2-oxo-oxazolidin-3-yl]-2-fluoro-phenyl}-piperazin-1-yl)-1-(2,4-difluoro-phenyl)-6-fluoro-4-oxo-1,4-dihydro-quinoline-3-carboxylic Acid

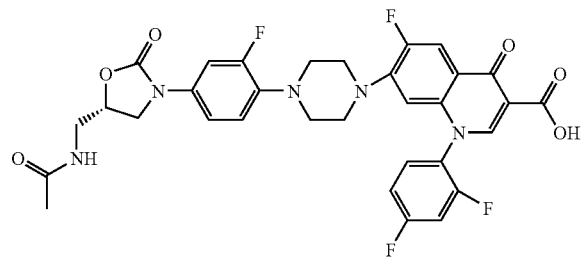

7-Chloro-1-(2,4-difluoro-phenyl)-6-fluoro-4-oxo-1,4-dihydro-quinoline-3-carboxylic Acid Ethyl Ester A solution of 2 g 2-(2,4-dichloro-5-fluoro-benzoyl)-3-ethoxy-acrylic acid ethyl ester (5.97 mmol) and 0.6 ml of 2,4-difluoroaniline (5.97 mmol) in 15 ml of ethanol was stirred at reflux for 25 hrs. The reaction was monitored by TLC. The ethanol was evaporated and the residual ethanol was distilled from an azeotrope with 20 ml heptane and 20 ml ethyl acetate. The yellow oil was dissolved in 20 ml of THF, reacted with 315 mg of a 50% NaH suspension in oil (6.56 mmol) and stirred at reflux for 20 hrs. The solution was diluted with ethyl acetate, washed with water and brine, dried over Mg sulfate, filtered and the filtrate evaporated.

Yield: 2.0 g, 90%. MW: 381.74, (C18H11ClF3NO3) MS: 382.3 (M+H)$^+$, Method ESI$^+$.

7-Chloro-1-(2,4-difluoro-phenyl)-6-fluoro-4-oxo-1,4-dihydro-quinoline-3-carboxylic Acid A mixture of 2.0 g of 7-chloro-1-(2,4-difluoro-phenyl)-6-fluoro-4-oxo-1,4-dihydro-quinoline-3-carboxylic acid ethyl ester (5.23 mmol) in 16 ml acetic acid and 16 ml HCl 37% was stirred 25 hrs at 90° C., and evaporated.

Yield: 1.71 g, quantitative. MW: 353.68, (C16H7ClF3NO3) MS: 354.3 (M+H)$^+$, Method ESI$^+$.

7-Chloro-1-(2,4-difluoro-phenyl)-6-fluoro-4-oxo-1,4-dihydro-quinoline-3-carboxylatoboron Diacetate To a stirred suspension of 1.71 g 7-chloro-1-(2,4-difluoro-phenyl)-6-fluoro-4-oxo-1,4-dihydro-quinoline-3-carboxylic acid (4.84 mmol) in 4 ml of dichloromethane were successively added at 0° C. 1.35 ml triethylamine (MW: 101.19, 9.68 mmol) and 0.517 ml acetyl chloride (MW: 78.50, d=1.1050, 7 26 mmol). The reaction mixture was allowed to warm up to RT, diluted with dichloromethane and washed twice with ice cold water and brine. The org. layer was dried with sodium sulfate, filtered and evaporated. The residue was crystallized from a dichloromethane/hexane mixture.

1.91 g of the colorless crystals were suspended in 3.21 ml of acetic anhydride (33.88 mmol), 400 mg anhydrous boric acid (6.47 mmol) and 5 mg zinc chloride (0.04 mmol) were added. The mixture was stirred at 80° C. for two hours. The reaction was poured on 10 g ice in 20 ml water and stirred. The colorless crystals were filtered, digested twice in 100 ml ethanol, filtered, washed with ether and hexane, and dried.

Yield: 1.7 g, 74%. MW: 481.58, (C20H12BClF3NO7) MS: 482.4 (M+H)$^+$, Method ESI$^+$.

7-(4-{(5S)-5-(Acetylamino-methyl)-2-oxo-oxazolidin-3-yl]-2-fluoro-phenyl}-piperazin-1-yl)-1-(2,4-difluoro-phenyl)-6-fluoro-4-oxo-1,4-dihydro-quinoline-3-carboxylic Acid A suspension of 240 mg of 7-chloro-1-(2,4-difluoro-phenyl)-6-fluoro-4-oxo-1,4-dihydro-quinoline-3-carboxylatoboron diacetate (0.5 mmol) and 336 mg N-({(5S)-3-[3-fluoro-4-(1-piperazinyl)phenyl]-2-oxo-5-oxazolidinyl}-methyl)-acetamide (1 mmol) in 2 ml DMSO were irradiated in a microwave oven for three 2.30 min periods at 250 W in a close reaction vessel under inert gas. The reaction was monitored by HPLC. The DMSO was evaporated and the residue was digested in acetonitrile/water. The solid was filtered off and the filtrate evaporated and purified by chromatography.

Yield: 11 mg, 4%. MW: 653.60, (C32H27F4N5O6) MS: 652.5 (M–H)$^-$, Method ESI$^-$.

Known building blocks
2,4-difluoroaniline: 367-25-9, Aldrich D10-140-0
2-(2,4-Dichloro-5-fluoro-benzoyl)-3-ethoxy-acrylic acid ethyl ester: 86483-52-5, WO0217916 A1 20020307

Example 7

7-(4-{4-[(5S)-5-(Acetylamino-methyl)-2-oxo-oxazolidin-3-yl]-2-fluoro-phenyl}-piperazin-1-yl)-1-cyclopropyl-8-methoxy-4-oxo-1,4-dihydro-quinoline-3-carboxylic Acid

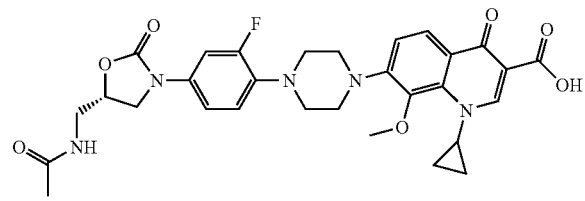

1-Cyclopropyl-7-fluoro-8-methoxy-4-oxo-1,4-dihydro-quinoline-3-carboxylatoboron Diacetate To a stirred suspension of 1.12 g of 1-cyclopropyl-7-fluoro-8-methoxy-4-oxo-1,4-dihydro-quinoline-3-carboxylic acid (4 mmol) in 20 ml of dichloromethane were successively added at 0° C. 1.2 ml triethylamine (8 mmol) and 0.454 ml acetyl chloride (MW: 78.50). The reaction mixture was allowed to warm up to RT, diluted with dichloromethane and washed twice with ice cold water and brine. The organic layer was dried with sodium sulfate, filtered and evaporated. The crystals were suspended in 3 ml of acetic anhydride (MW: 102.9, 28 mmol) and 354 mg anhydrous boric acid (MW: 61.83, 5.6 mmol) and 10 mg zinc chloride (MW: 136.28, 0.07 mmol) were added. The mixture was stirred at 80° C. for two hours. The reaction was poured on 10 g ice in 20 ml water and stirred. The colorless crystals were filtered.

Yield: 600 mg, 46%. MW: 405.14, (C18H17BFNO8) MS: 406.5, (M+H)$^+$, Method ESI$^+$.

7-(4-{4-[(5S)-5-(Acetylamino-methyl)-2-oxo-oxazolidin-3-yl]-2-fluoro-phenyl}-piperazin-1-yl)-1-cyclopropyl-8-methoxy-4-oxo-1,4-dihydro-quinoline-3-carboxylic Acid A solution of 100 mg 1-cyclopropyl-7-fluoro-8-methoxy-4-oxo-1,4-dihydro-quinoline-3-carboxylatoboron diacetate (0.24 mmol), 166 mg of N-[[3-[(5S)-3-fluoro-4-(1-piperazinyl)phenyl]-2-oxo-5-oxazolidinyl]methyl]-acetamide (0.49 mmol) and 59 μl ethyldiisopropylamine (0.336 mmol) in 1 ml DMSO was irradiated in a microwave oven for 10 min at 150° C. The reaction was monitored by HPLC. The DMSO was evaporated and the residue was purified by chromatography using a CH$_2$Cl$_2$/MeOH 5% mixture.

Yield: 14 mg, 10%. MW: 593.62, (C30H32FN5O7). MS: 594.6 (M+H)$^+$, Method ESI$^+$.

Known building blocks
1-Cyclopropyl-7-fluoro-8-methoxy-4-oxo-1,4-dihydro-quinoline-3-carboxylic acid: 221221-16-5, U.S. Pat. No. 6,329,391
N-[[3-[3-fluoro-4-(1-piperazinyl)phenyl]-2-oxo-5-oxazolidinyl]methyl]-acetamide: 154590-43-9, U.S. Pat. No. 5,547,950

Example 8

9-(4-{4-[(5S)-5-(Acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic Acid

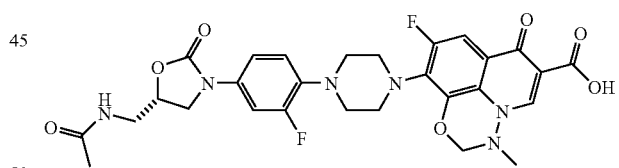

9-(4-{4-[(5S)-5-(Acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic Acid Ethyl Ester A solution of 100 mg 8,9-difluoro-3-methyl-6-oxo-2,3-dihydro-6H-1-oxa-3,3a-diaza-phenalene-5-carboxylic acid ethyl ester (0.32 mmol) and 216 mg of N-[{(5S)-3[3-fluoro-4-(1-piperazinyl)phenyl]-2-oxo-5-oxazolidinyl}-methyl]-acetamide (0.64 mmol) were dissolved in a mixture of 1 ml pyridine and 1 ml DMSO. The reaction was monitored by TLC. The DMSO was evaporated, the residue digested in water and the solid collected. The solid was purified by chromatography, using a 9/1 dichloromethane/methanol mixture as eluent.

Yield: 44 mg 22%. MW: 626.62, (C30H32F2N6O7) MS: 627.7 (M+H)+, Method ESI+.

9-(4-{4-[(5S)-5-(Acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic Acid 44 mg of 9-(4-{4-[(5S)-5-(acetylamino-methyl)-2-oxo-oxazolidin-3-yl]-2-fluoro-phenyl}-piperazin-1-yl)-8-fluoro-3-methyl-6-oxo-2,3-dihydro-6H-1-oxa-3,3a-diaza-phenalene-5-carboxylic acid ethyl ester (0.32 mmol) were heated at 80° C. in 2 ml of a 1/1 conc. HCl and acetic acid mixture. The reaction was monitored by HPLC. The HCl/AcOH mixture was evaporated, the residue dissolved in a methanol/dichloromethane 1/1 mixture, treated with triethylamine and evaporated. The deacetylated residue was dissolved in a 1/1 mixture acetic acid and acetic anhydride, and the reaction monitored by HPLC. The solvents were evaporated and the residue was purified by preparative HPLC.

Yield: 9.1 mg 21%. MW: 598.56, (C28H28F2N6O7) MS: 599.2 (M+H)+, 597.7 (M−H)−, Method ESI+, ESI−.

Example 9

7-{(3RS)-3-[({4-[(5S)-5-(Acetylamino-methyl)-2-oxo-oxazolidin-3-yl]-2-fluoro-phenyl}-ethyl-amino)methyl]-piperazin-1-yl}-1-cyclopropyl-6-fluoro-4-oxo-1,4-dihydro-quinoline-3-carboxylic Acid

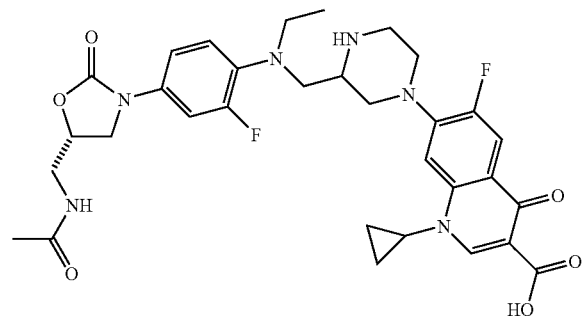

(1,4-Dibenzyl-piperazin-2-ylmethylen)-ethyl-amine

To a solution of 0.5 g (1,4-bis(phenylmethyl)-2-piperazincarboxaldehyd in 5 ml of dichloromethane was added 0.54 ml ethylamine and 0.5 g molecular sieves. The reaction mixture was stirred for 30 min at rt then filtered. The filtrate was evaporated to dryness.

Yield: 385 mg, 71%. MW: 321.46, (C21H27N3)

1H-NMR (400 MHz, D6-DMSO; δ ppm): 1.07 (t, 3H, N—CH2-CH3); 2.07-2.22 (m, 3H, N—CH2); 2.63-2.73 (m, 3H, N—CH2) 2.92 (m, 1H, pip.H2); 3.25-3.74 (AB, 2H, CH2-Ph); 3.41-3.53 (AB, 2H, CH2-Ph); 7.22-7.35 (m, 10H, Ph); 7.6 (d, 1H, methylene).

[(2R,S)-(1,4-Dibenzyl-piperazin-2-ylmethyl)]-ethyl-amine 0.92 g of sodium borohydride were added to a stirred solution of 5.24 g of [(2R,S)-1,4-dibenzyl-piperazin-2-ylmethylen]-ethylamine in 50 ml dry THF and 3 ml ethanol under inert gas. The reaction mixture was stirred at rt for 6 hrs. Second and third portions of 0.92 g of sodium borohydride were added after 8 and 12 hrs respectively. The reaction was quenched with 20 ml of HCl 0.1M. The reaction mixture was diluted with ethyl acetate and the organic layer was washed with water and brine, dried over MgSO4, filtered and the filtrate evaporated to give 5.5 g of an oil. The oil was purified by chromatography over SiO2 with a 1/1 hexane/acetone mixture with 1% triethylamine.

Yield: 2.1 g, 40%. MW: 323.48, (C21H29N3)

1H-NMR (400 MHz, D6-DMSO; δ ppm): 0.91 (t, 3H, N—CH2-CH3); 2.07-2.23 (m, 3H, N—CH2); 2.38-2.52 (m, 4H, N—CH2); 2.60-2.70 (m, 4H, N—CH, N—CH2); 3.21-3.26 and 3.97-4.01 (AB, 2H, CH2-Ph); 3.36-3.47 (AB, 2H, CH2-Ph); 7.18-7.33 (m, 10H, Ph-H).

[(2R,S)-1,4-Dibenzyl-piperazin-2-ylmethyl]-ethyl-(2-fluoro-4-nitro-phenyl)-amine A mixture of 1.057 g of 3,4-difluoro-nitrobenzene (6.34 mmol), 2.05 g [(2R,S)1,4-dibenzyl-piperazin-2-ylmethyl]-ethylamine (6.34 mmol) and 1.4 ml triethylamine (9.9 mmol) in 10 ml of ethyl acetate was stirred at 60° C. The reaction was monitored by TLC. The reaction was diluted with ethyl acetate, washed with water and brine, dried over Mg sulfate and filtered. The filtrate was evaporated and the residue was purified by chromatography using an ethyl acetate/hexane 3/7 mixture as eluent. The interesting fractions were collected and evaporated to leave a yellow sticky oil.

Yield: 2.58 g, 88%. MW: 462.57, (C27H31FN4O2) MS: 463.3 (M+H)+, Method ESI+.

(4-[{(2R,S)-1,4-Dibenzyl-piperazin-2-ylmethyl}-ethyl-amino]-3-fluoro-phenyl)-carbamic Acid Benzyl Ester To a solution of 2.58 g ((2R,S)-1,4-dibenzyl-piperazin-2-ylmethyl)-ethyl-(2-fluoro-4-nitro-phenyl)-amine in 100 ml methanol was sequentially added 50 ml of a saturated solution of ammonium chloride in water and 0.5 g zinc dust. The mixture was vigorously stirred and monitored by TLC. The solid was filtered, the filtrate concentrated and the solid deep red material filtered from the aqueous layer. The solid was dissolved in ethyl acetate, washed twice with water and brine, dried over Mg sulfate, filtered and evaporated.

The deep red oily residue was dissolved in 100 ml acetone. 50 ml of saturated sodium bicarbonate solution was added. Under vigorous stirring, 1.17 ml of benzylchloroformate were added at 0° C. The reaction was stirred at rt over night, the acetone evaporated and the water layer extracted twice with ethyl acetate. The org. layer was washed with water and brine, dried over Mg SO4, filtered and the filtrate evaporated. The residue was purified by chromatography, using a 95/5 dichloromethane/methanol mixture as eluent.

Yield: 3.1 g, quantitative. MW: 566.72, (C35H39FN4O2)

1H-NMR (400 MHz, D6-DMSO; δ ppm): 0.95 (t, 3H, N—CH2-CH3); 2.26-2.39 (m, 3H, N—CH2); 2.55-2.70 (m, 2H, N—CH2); 2.99-3.05 (m, 2H, N—CH2); 3.18-3.25 (m, 1H, N—CH2); 3.43-3.50 (m, 3H, —NH2); 4.04-5.25 and 4.54-5.20 (AB, 4H, CH2-Ph); 3.36-3.47 (AB, 2H, CH2-Ph); 6.96-7.07 (t, 1H, Ph-H); 7.09-7.12 (dd, 1H, Ph-H); 7.23-7.49 (m, 16H, Ph-H); 9.82 (s, 1H, N—H).

(5R)-3-{4-[{(2R,S)-1,4-Dibenzyl-piperazin-2-ylmethyl}-ethyl-amino]-3-fluoro-phenyl}-5-hydroxymethyl-oxazolidin-2-one To a solution of 3.1 g (4-[{(2R,S)-1,4-dibenzyl-piperazin-2-ylmethyl}-ethyl-amino]-3-fluoro-phenyl)-carbamic acid benzyl ester (5.4 mmol) in 25 ml THF at −78° C. was added dropwise 4.38 ml of a butyl-lithium solution (1.6M, 7 mmol) in N-hexane. The mixture was stirred at −78° C. for 10 min, than allowed to reach −40° C. for 10 min. 1.28 g of R(−)-glycidyl butyrate (8.92 mmol) was added. The reaction was allowed to reach 20° C. and was monitored by TLC. The reaction was diluted with ethyl acetate, washed with water and brine, dried over Mg sulfate, filtered and the filtrate evaporated. The residue was purified by chromatography, using a 92.5/7.5 dichloromethane/methanol mixture as eluent.

Yield: 2.35 g 69%. MW: 532.68, (C31H37FN4O3) MS: 533.1 (M+H)+, Method ESI+.

Methanesulfonic Acid (5R)-3-{4-[{(2R,S)-1,4-Dibenzyl-piperazin-2-ylmethyl}-ethyl-amino]-3-fluoro-phenyl}-2-oxo-oxazolidin-5-ylmethyl Ester To a solution of 1.2 g of (5R)-3-{4-[{(2R,S)-1,4-dibenzyl-piperazin-2-ylmethyl}-ethyl-amino]-3-fluoro-phenyl}-5-hydroxymethyl-oxazolidin-2-one (2.25 mmol) and 0.5 ml of triethylamine (4.5 mmol) in 10 ml of dichloromethane was added at 0° C. 0.272 g of methansulfonyl chloride (2.4 mmol). The reaction was stirred at 25° C. and monitored by TLC. The reaction was quenched with water, the org. layer washed with water and brine, dried over Mg sulfate, filtered and the filtrate evaporated. The oily residue was purified by chromatography using a 95/5 dichloromethane/methanol mixture with 0.5% triethylamine. The fractions with a rf of 0.18 were collected and evaporated.

Yield: 1.02 g, 75%, MW: 610.75, (C32H39FN4O5S) MS: 611.1 (M+H)+, Method ESI+.

(5R)-5-Azidomethyl-3-{4-[{(2R,S)-1,4-Dibenzyl-piperazin-2-ylmethyl}-ethyl-amino]-3-fluoro-phenyl}-oxazolidin-2-one A suspension of 1.16 g of methanesulfonic acid-(5R)-3-{4-[{(2R,S)-1,4-dibenzyl-piperazin-2-ylmethyl}-ethyl-amino]-3-fluoro-phenyl}-2-oxo-oxazolidin-5-ylmethyl ester (1.89 mmol), 0.245 mg sodium azide (MW: 65.01, 3.7 mmol) and 29 mg of sodium iodide (0.0189 mmol) in 5 ml of DMF was stirred under inert gas at 80° C. The reaction was monitored by TLC. The DMF was evaporated, the residue dissolved in ethyl acetate, washed with water and brine, dried over Mg sulfate than filtered and the filtrate evaporated. The oily residue was purified by chromatography using a 95/5 dichloromethane/methanol mixture with 0.25% triethylamine as eluent. The fractions with a rf of 0.19 were collected and dried.

Yield: 0.89 g, 84%. MW: 557.67, (C31H36FN7O2) MS: 558.3 (M+H)+, Method ESI+.

N-[(5S)-3-{4-[{(2R,S)-(1,4-Dibenzyl-piperazin-2-ylmethyl}-ethyl-amino]-3-fluoro-phenyl}-2-oxo-oxazolidin-5-ylmethyl]-acetamide A solution of 889 mg (5R)-5-azidomethyl-3-{4-[{(2R,S)-1,4-dibenzyl-piperazin-2-ylmethyl}-ethyl-amino]-3-fluoro-phenyl}-oxazolidin-2-one (1.59 mmol), 459 mg triphenylphosphine (1.75 mmol) and 286 mg water (15.94 mmol) in 20 ml of THF was stirred at 50° C. for 22 hrs. The reaction was monitored by TLC. The THF was evaporated and the residue dissolved in 2 ml acetic anhydride. The reaction was monitored by TLC. The solvent was evaporated and the residue was purified by chromatography using a 95/5 dichloromethane/methanol mixture with 0.5% triethylamine as eluent leaving a sticky oil.

Yield: 0.6 g, 65%. MW: 573.71, (C33H40FN5O3) MS: 574.2 (M+H)+, Method ESI+.

N-[(5S)-3-{4-[{(2R,S)-piperazin-2-ylmethyl}-ethyl-amino]-3-fluoro-phenyl}-2-oxo-oxazolidin-5-ylmethyl]-acetamide A suspension of 0.59 g N-[(5S)-3-{4-[{(2R,S)-(1,4-dibenzyl-piperazin-2-ylmethyl}-ethyl-amino]-3-fluoro-phenyl}-2-oxo-oxazolidin-5-ylmethyl]-acetamide (1.028 mmol) and 300 mg Pd/C in 20 ml of a 1/1 ethyl acetate/methanol mixture was stirred under H2 at room temperature. The reaction was monitored by TLC. The Pd/C was filtered and the filtrate evaporated to dryness. The glassy residue was dried.

Yield: 0.3 g, 86%. MW: 393.46, (C19H28FN5O3) MS: 394.3 (M+H), Method ESI+.

7-{(3R,S)-3-[({4-[(5S)-5-(Acetylamino-methyl)-2-oxo-oxazolidin-3-yl]-2-fluoro-phenyl}-ethyl-amino)methyl]-piperazin-1-yl}-1-cyclopropyl-6-fluoro-4-oxo-1,4-dihydro-quinoline-3-carboxylic Acid A suspension of 115 mg of 7-chloro-6-fluoro-1-cyclopropyl-4-oxo-1,4-dihydroquinoline-3-carboxylatoboron diacetate (0.282 mmol), 100 mg N-[(5S)-3-{4-[{(2R,S)-piperazin-2-ylmethyl}-ethyl-amino]-3-fluoro-phenyl}-2-oxo-oxazolidin-5-ylmethyl]-acetamide and 35 mg DABCO in 1 ml DMSO was heated in a micro wave oven for 10 periods of 2.5 min. at 240 W. The reaction was monitored by TLC. The DMSO was evaporated, the residue dissolved in 10 ml dichloromethane and the solid collected. The solid was digested in 3 ml water, filtered and purified by prep HPLC. The fractions were concentrated by evaporation and the water freezed dried.

Yield: 13.5 mg, 7.6%. MW: 638.67, (C32H36F2N6O6) MS: 639.4 (M+H)+, Method ESI+.

Known building block:
(1,4-Bis(phenylmethyl)-2-piperazincarboxaldehyde
Lit. Naylor Alan and all. Eur. Pat. Appl (1989), EP 343900

Example 10

7-(4-{[(5S)-5-(Acetylamino-methyl)-2-oxo-oxazolidin-3-yl]-2-fluoro-phenyl}-piperazin-1-yl)-1-cyclopropyl-6-fluoro-4-oxo-1,4-dihydro-[1,8]naphthyridine-3-carboxylic Acid

7-(4-{[(5S)-5-(Acetylamino-methyl)-2-oxo-oxazolidin-3-yl]-2-fluoro-phenyl}-piperazin-1-yl)-1-cyclopropyl-6-fluoro-4-oxo-1,4-dihydro-[1,8]naphthyridine-3-carboxylic Acid A suspension of 100 mg 7-chloro-1-cyclopropyl-6-fluoro-1,4-dihydro-4-oxo-[1,8]naphthyridine-3-carboxylic acid 0.35 mmol), 130 mg N-[{(5S)-3[3-fluoro-4-(1-piperazinyl)phenyl]-2-oxo-5-oxazolidinyl}methyl]-acetamide (0.39 mmol) 119 mg triethylamine (MW: 101.19, 1.17 mmol) and 85 mg trimethylchlorsilan (0-78 mmol) in 2 μl DMSO was heated at 150° C. under stirring in a microwave oven for 10 min. The reaction was monitored by TLC. The DMSO was evaporated, the residue digested in water, filtered and the solid purified by chromatography, using dichloromethane/methanol mixture as eluent. The fractions were collected and evaporated. The residue was crystallized from acetonitrile.

Yield: 84 mg, 42%. MW: 582.57, (C28H28F2N6O6) MS: 583.3 (M+H)$^+$, 581.6 (M+H)$^-$ Method ESI$^+$, ESI$^-$.

Known building blocks
7-chloro-1-cyclopropyl-6-fluoro-1,4-dihydro-4-oxo-[1,8]naphthyridine-3-carboxylic acid
Lit.: U.S. Pat. No. 4,777,175; U.S. Pat. No. 5,281,612; CAS: 100361-18-0
N-[{(5S)-3[3-fluoro-4-(1-piperazinyl)phenyl]-2-oxo-5-oxazolidinyl}methyl]-acetamide
Lit. U.S. Pat. No. 5,547,950 CAS: 154590-66-6

Example 11

7-{4-[2-(4-{4-[5-(Acetylamino-methyl)-2-oxo-oxazolidin-3-yl]-2-fluoro-phenyl}-piperazin-1-yl)-ethyl]-piperazin-1-yl}-1-cyclopropyl-6-fluoro-4-oxo-1,4-dihydro-quinoline-3-carboxylic Acid

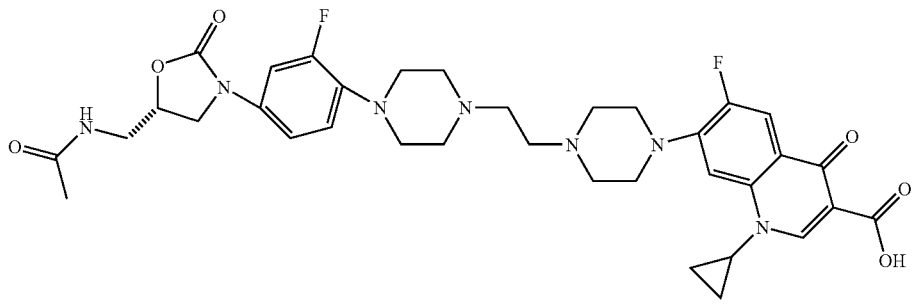

4-[2-(4-{4-[(5S)-5-(Acetylamino-methyl)-2-oxo-oxazolidin-3-yl]-2-fluoro-phenyl}-piperazine1-yl)ethyl]piperazine-1-carboxylic Acid Tert Butyl Ester A solution of 336 mg of N-({(5S)-3-[-3-fluoro-4-(1-piperazinyl)phenyl]-2-oxo-5-oxazolidinyl}methyl)-acetamide (1 mmol), 308 mg of 4-[2-{2-(methylsulfonyl)-oxy}-ethyl]-1-piperazinecarboxylic acid-1,1-dimethylethyl ester (1 mmol), 32.2 mg of tetrabutylammonium iodide (0.08 mmol) and 203 mg of potassium carbonate (2.5 mmol) in 2 ml DMF was stirred at 80° for 20 h. The solvent was evaporated and the residue purified by prep HPLC.

Yield: 200 mg, 36%. C27H41FN6O5 (Mw: 548.6) MS: (M+H)$^+$ 549.5, Method ESI$^+$.

N-[(5S)-3-{3-Fluoro-4-[4-(2-piperazin-1-yl-ethyl)-piperazin-1-yl]-phenyl}-2-oxo-oxazolidin-5ylmethyl]-acetamide A solution of 200 mg of 4-[2-(4-{4-[(5S)-5-(acetylaminomethyl)-2-oxo-oxazolidin-3-yl]-2-fluoro-phenyl}-piperazine-1-yl)ethyl]piperazine-1-carboxylic acid tert butyl ester (0.36 mmol) in 2 ml dichloromethane and 2 ml trifluoracetic acid was stirred for 10 min. The solvents were evaporated, the residue was digested in ether and the solid filtered. The solid was dissolved in water and neutralized with a saturated solution of sodium bicarbonate. The water was evaporated and the product dried as a mixture with the salts.

Yield: 136 mg, 100%. C22H33FN6O3 (Mw: 448.5) MS: 449.4 (M+H)$^+$, Method ESI$^+$.

6,7-Difluoro-1-cyclopropyl-4-oxo-1,4-dihydroquinoline-3-carboxylatoboron Diacetate To a suspension of 2 g of 1-cyclopropyl-6,7 difluoro-1,4-dihydro-4-oxo-3-quinolinecarboxylic acid (0.754 mmol) in 30 ml dichloromethane was added at 0° C., 2.10 ml triethylamine (1.52 mmol) and 804 μl acetyl chloride (1.1 mmol). The solution was allowed warm up to RT. The mixture was then diluted with dichloromethane and washed twice with water and brine. The organic layer was dried over MG sulfate, filtered and the filtrate evaporated. The solid was suspended in 5.08 ml of acetic anhydride (5.2 mmol), 628 mg anhydrous boric acid (MW: 61.83, 1 mmol) and 20 mg zinc chloride (0.14 mmol) were added. The mixture was stirred at 80° C. for 20 hrs. The reaction was poured on 10-g ice in 20 ml water and stirred. The solid was filtered.

Yield: 1.4 g 47%. C17H14BF2NO7 (Mw: 393.1) MS: 394.1 (M+H)$^+$, Method ESI$^+$.

7-{4-[2-(4-{4-[(5S)-5-(Acetylamino-methyl)-2-oxo-oxalidin-3-yl]-2-fluoro-phenyl}-piperazin-1yl)-ethyl]-piperazin-1-yl}-1-cyclopropyl-6-fluoro-4-oxo-1,4-dihydro-quinoline-3-carboxylic Acid A mixture of 163 mg of N-[(5S)-3-{3-fluoro-4-[4-(2-piperazin-1-yl-ethyl)-piperazin-1-yl]-phenyl}-2-oxo-oxazolidin-5ylmethyl]-acetamide (0.36 mmol), 142.85 mg of 6,7-difluoro-1-cyclopropyl-4-oxo-1,4-dihydroquinoline-3-carboxylatoboron diacetate (0.36 mmol) and 44.77 mg DABCO (0.36 mmol) was irradiated in a micro wave oven for three periods of 3 min. The reaction was followed with HPLC. DMSO was evaporated and the residue purified by preparative HPLC.

Yield: 40 mg, 16%. C35H41F2N7O6; (Mw: 693.7) MS: 694.3(M+H)$^+$, 692.6 (M–H)$^-$, Method ESI$^+$, Method ESI$^-$.

Known building blocks:
1-piperazinecarboxylic acid, 4-[2-[2-[methylsulfonyl) oxy]-ethyl]-1-piperazinecarboxylic acid-1,1-dimethylethyl ester: WO 8808424
1-cyclopropyl-6,7 difluoro-1,4-dihydro-4-oxo-3-quinoline-carboxylic acid: EP 1160241
N-[[3-[3-fluoro-4-(1-piperazinyl)phenyl]-2-oxo-5-oxazo-lidinyl]methyl]-acetamide: 154590-43-9: U.S. Pat. No. 5,547,950

Example 12

7-[4-(4-{4-[(5S)-5-(Acetylamino-methyl)-2-oxo-oxazolidin-3-yl]-2-fluoro-phenyl}-piperazin-1-yl)-piperidin-1-yl]-1-cyclopropyl-6-fluoro-4-oxo-1,4-dihydro-quinoline-3-carboxylic Acid

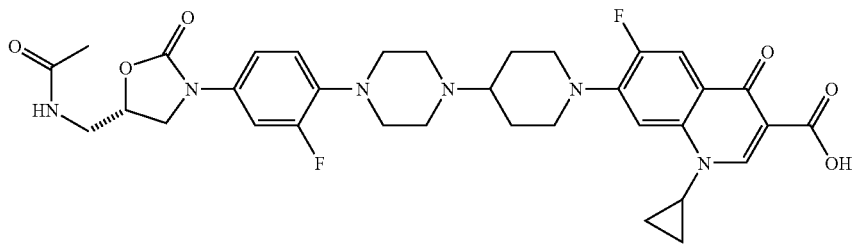

1-(1-Benzyl-piperidin-4-yl)-4-(2-fluoro-4-nitro-phenyl)-piperazine

To a solution of 10 g of 2,2-[(2-fluoro-4-nitrophenyl)-imino]bis-ethanol (40.5 mmol) and 12.3 g triethylamine (120 mmol) in 200 ml dichloromethane at 0° C. were added 11.12 g methane sulfonylchloride (97.3 mmol). The reaction mixture was stirred at rt and monitored by TLC. The mixture was diluted with 50 ml dichloromethane, washed with water, sodium bicarbonate solution and brine at 0° C. The org. layer was dried over Mg sulfate, filtered and the filtrate evaporated to leave a yellow solid. The solid was dissolved in 200 ml toluene and 8.48 g 4-amino-1-benzylpiperidine and 16.9 ml triethylamine were added. The suspension was stirred at 120° C. for 72 hrs. The reaction was monitored by TLC. The solvents were evaporated, the residue dissolved in ethyl acetate, washed with water and brine, dried over MG sulfate, filtered and evaporated. The residue was purified by chromatography, using a 9/1 dichloromethane/methanol mixture as eluent. The interesting fractions were collected and evaporated. The residue was crystallized from ethyl acetate/hexane mixture.

Yield: 6.05 g, 40%. MW: 398.48, (C22H27FN4O2) MS: 399.4 (M+H)+, Method ESI+.

4-[4-(4-Benzyloxycarbonylamino-2-fluoro-phenyl)-piperazin-1yl]-piperidine-1-carboxylic Benzyl Ester To a solution of 6.05 g 1-(1-benzyl-piperidin-4-yl)-4-(2-fluoro-4-nitro-phenyl)-piperazine (15.2 mmol) 50 ml methanol and 5 ml acetic acid was added 2 g of Pd/C 10%. The suspension was stirred mechanically under hydrogen. The reaction was monitored by TLC. The Pd/C was filtered, the filtrate evaporated to dryness. The residue was dissolved in 250 ml acetone, diluted with 125 ml of a saturated solution of sodium bicarbonate, and reacted with 8 ml of benzyl chloroformate. The reaction was monitored by TLC. The acetone was evaporated, the sticky oil dissolved in ethyl acetate, washed with water and brine and dried over Mg sulfate. The Mg sulfate was filtered and the filtrate evaporated to dryness. The residue was crystallized from an ethyl acetate/hexane mixture.

Yield: 6.40 g, 77%. MW: 546.64, (C31H35FN4O4) MS: 547.4 (M+H)+, Method ESI+.

4-{4-[2-fluoro-4{(5R)-5-hydroxymethyl-2-oxo-oxazolidin-3-yl}-phenyl]-piperazin-1-yl}-piperidin-1-carboxylic Acid Benzyl Ester To a solution of 6.3 g 4-[4-(4-benzyloxycarbonylamino-2-fluoro-phenyl)-piperazin-1-yl]-piperidine-1-carboxylic benzyl ester (11.52 mmol) in 60 ml of dry THF were added at −20° C. under stirring 5.7 ml of a 2.25 M LDA solution (12.8 mmol) in THF. The reaction was allowed to warm up to 0° C., and 2.1 ml of R(−)-glycidyl butyrate (14.9 mmol) were added. The reaction was stirred at rt. and monitored by TLC. The reaction was quenched with ammonium chloride solution, diluted with water, and the org. layer was washed with 10% sodium bicarbonate solution and brine. The org. layer was dried over Mg sulfate and filtered. The filtrate was evaporated to dryness, and the residue crystallized from an ethyl acetate/hexane mixture.

Yield: 3.87 g, 65.5%. MW: 512.58, (C27H33FN4O5) MS: 513.7 (M+H)+, Method ESI+.

4-{4-[4-{(5R)-5-Azidomethyl-2-oxo-oxazolidin-3-yl}-2-fluoro-phenyl]-piperazin-1-yl}-piperidin-1-carboxylic Acid Benzyl Ester To a solution of 3.67 g 4-{4-[2-fluoro-4{(5R)-5-hydroxymethyl-2-oxo-oxazolidin-3-yl}-phenyl]-piperazin-1-yl}-piperidin-1-carboxylic acid benzyl ester (7.16 mmol) and 1.99 ml of triethylamine (14.3 mmol) in 50 ml dichloromethane was added at 0° C. 0.66 ml of methansulfonyl chloride (8.59 mmol). The reaction was stirred at room temperature and monitored by TLC. The reaction was diluted with water and washed with water and brine. The org. layer was dried over Mg sulfate, filtered and evaporated. The oily residue was dissolved in 15 ml DMF. 100 mg of tetrabutyl ammonium iodide and 0.930 g sodium azide (14.32 mmol) were added and the mixture stirred under nitrogen at 80° C. The reaction was monitored by TLC. The DMF was evaporated, the residue dissolved in ethyl acetate and washed with water and brine. The org. layer was dried over Mg sulfate, filtered and evaporated. The residue was crystallized from an ethyl acetate/ether mixture.

Yield: 2.65 g, 69%. MW: 537.59, (C27H32FN7O4) MS: 538.8 (M+H)+, Method ESI+.

4-(4-{4-[(5S)-5-(Acetylamino-methyl)-2-oxo-oxazolidin-3-yl]-2-fluoro-phenyl}-piperazin-1-yl)-piperidin-1-carboxylic Acid Benzyl Ester A solution of 2.65 g of 4-{4-[4-{(5R)-5-azidomethyl-2-oxo-oxazolidin-3-yl}-2-fluoro-phenyl]-piperazin-1-yl}-piperidin-1-carboxylic acid benzyl ester (4.93 mmol), 1.55 g triphenylphosphine (5.91 mmol) and 0.88 g water (49.3 mmol) in 40 ml THF was stirred at reflux for 22 hrs. The reaction was controlled by TLC. The THF was evaporated and the residue dissolved in 10 ml acetic acid and 2 ml of acetic anhydride. the reaction was monitored by TLC. The solvents were evaporated and the residue crystallized from ethyl acetate.

Yield: 2.57 g, 94%. MW: 553.63, (C29H36FN5O5) MS: 554.5 (M+H)⁺, Method ESI⁺.

N-{(5S)-3-[3-Fluoro-4-(4-piperidin-4-yl-piperazin-1-yl)-phenyl]-2-oxo-oxazolidin-5-ylmethyl}-acetamide A suspension of 500 mg of 10% Pd/C and 2.5 g 4-(4-{4-[((5R)-5-(acetylamino-methyl)-2-oxo-oxazolidin-3-yl]-2-fluoro-phenyl}-piperazin-1-yl)-piperidin-1-carboxylic acid benzyl ester (5.51 mmol) in 50 ml methanol was stirred under hydrogen. The reaction was monitored by TLC. The Pd/C was filtered off, the filtrate evaporated to dryness and the residue digested in an ethyl acetate/hexane mixture. The glassy solid was filtered, washed with hexane and dried.

Yield: 1.805 g, 78%. MW: 419.50, (C21H30FN5O3) MS: 420.5 (M+H)⁺, Method ESI⁺.

7-[4-(4-{4-[(5S)-5-(Acetylamino-methyl)-2-oxo-oxazolidin-3-yl]-2-fluoro-phenyl}-piperazin-1-yl)-piperidin-1-yl]-1-cyclopropyl-6-fluoro-4-oxo-1,4-dihydro-quinoline-3-carboxylic Acid A suspension of 130 mg 6,7-difluoro-1-cyclopropyl-4-oxo-1,4-dihydroquinoline-3-carboxylatoboron diacetate (0.33 mmol), 147 mg N-{3-[3-fluoro-4-(4-piperidin-4-yl-piperazin-1-yl)-phenyl]-2-oxo-oxazolidin-5-ylmethyl}-acetamide (0.35 mmol) and 56 mg DABCO (0.5 mmol) in 10 ml acetonitrile were heated under stirring in a micro wave oven at 150° C. for 10 min. The solvents were evaporated, the residue digested over night in ethanol and the solid filtered off. The solid was digested in a 4/1 mixture of methanol/1N HCl and the solid filtered.

Yield: 65 mg, 29%. MW: 664.72, (C34H38F2N6O6) MS: 665.5 (M+H)⁺, 663.4 (M−H)⁻ Method ESI⁺, ESI⁻.

Example 13

7-[(3R,4R) and (3S,4S)-3-{4-[(5S)-5-(Acetylamino-methyl)-2-oxo-oxazolidin-3-yl]-2-fluoro-phenyl}-4-aminomethyl-pyrrolidin-1-yl]-1-cyclopropyl-6-fluoro-4-oxo-1,4-dihydro-quinolin-3-carboxylic Acid

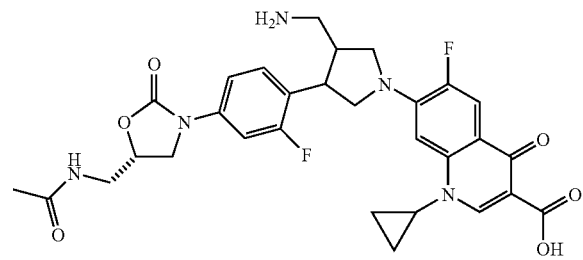

(4-Bromo-3-fluoro-phenyl)-carbamic Acid Benzyl Ester

To a solution of 10 g of 4-bromo-3-fluoroaniline (52 mmol) in 300 ml acetone were added successively 150 ml of a saturated sodium bicarbonate solution and at 0° C. 9 ml of benzyl chloroformate (63 mmol). The reaction was monitored by TLC. The acetone was evaporated, the residue extracted twice with ethyl acetate, washed with water and brine, dried and evaporated. The residue was crystallized from an ethyl acetate/hexane mixture.

Yield: 15.7 g, 92%. MW: 324.15, (C14H11BrFNO2) MS: 322.4 (M−H)⁻ Method ESI⁻.

3-(4-Benzyloxycarbonylamino-2-fluoro-phenyl)-acrylic Acid Ethyl Ester

A suspension of 9.72 g (4-bromo-3-fluoro-phenyl)-carbamic acid benzyl ester (30 mmol), 6 g ethyl acrylate (60 mmol), 10.2 ml DIPEA (60 mmol), 112 mg palladium acetate (3 mmol), and 1.57 g triphenylphosphine (6 mmol) in 10 ml DMF were stirred at 130° C. for 48 h. The reaction was monitored by TLC. The DMF was evaporated, the residue dissolved in dichloromethane, washed with water and brine, dried over Mg sulfate, filtered and the filtrate evaporated. The residue was purified by chromatography, using a 7/3 N-hexane/ethyl acetate mixture as eluent.

Yield: 4.50 g, 43%. MW: 343.35, (C19H18FNO4) MS: 342.1 (M−H)⁻ Method ESI⁻.

(3S,4R) and (3R,4S)-1-Benzyl-4-(4-benzyloxycarbonylamino-2-fluoro-phenyl)-pyrrolidine-3-carboxylic Acid Ethyl Ester To a solution of 4.5 g of 3-(4-benzyloxycarbonylamino-2-fluoro-phenyl)-acrylic acid ethyl ester (13.1 mmol) and 7.68 g N-[(pentyloxy)methyl]-N-[(trimethylsilyl)-methyl]-benzenemethanamine (26.2 mmol) in 50 ml dichloromethane was added 10 µL. trifluoroacetic acid. The reaction was monitored by TLC. The reaction was complete after 10 min. The mixture was diluted with dichloromethane, washed with sat. sodium bicarbonate solution and brine, dried over Mg sulfate, filtered and the filtrate evaporated. The residue was purified by filtration over a short silica column, using a 7/3 hexane/ethyl acetate mixture as eluent.

Yield: 4.93 g, 79%. MW: 476.55, (C28H29FN2O4) MS: 477.4 (M+H)⁺ Method ESI⁺.

[4-{(3R,4S) and (3S,4R)-1-Benzyl-4-hydroxymethyl-pyrrolidin-3-yl}-3-fluoro-phenyl]-carbamic Acid Benzyl Ester A solution of 4.05 g (3R,4S) and (3S,4R)-1-benzyl-4-(4-benzyloxycarbonylamino-2-fluoro-phenyl)-pyrrolidine-3-carboxylic acid ethyl ester (10.3 mmol) in 10 ml ether was added to a suspension of 480 mg LAH (15.5 mmol) in 100 ml diethylether at RT. The reaction was monitored by TLC. The excess LAH was hydrolyzed by a saturated sodium/potassium tartrate salt solution. The reaction was diluted with ethyl acetate, washed with water and brine, dried over Mg sulfate, filtered and the filtrate evaporated to dryness. The residue was crystallized from an ethyl acetate/hexane mixture.

Yield: 4.93 g, 79%. MW: 434.51, (C26H27FN2O3) MS: 435.6 (M+H)⁺ Method ESI⁺.

[4-{(3R,4S) and (3S,4R)-4-Azidomethyl-1-benzyl-pyrolidin-3-yl}-3-fluoro-phenyl]-carbamic Acid Benzyl Ester This compound was synthesized in analogy to the procedure described in Example 12 with 4.73 g [4-{(3R,4S) and (3S,4R)-1-benzyl-4-hydroxymethyl-pyrrolidin-3-yl}-3-fluoro-phenyl]-carbamic acid benzyl ester (10.9 mmol).

Yield: 5.0 g, quantitative. MW: 459.52, (C26H26FN5O2) MS: 460.6 (M+H)+ Method ESI+.

{4-[(3R,4S) and (3S,4R)-1-Benzyl-4(tert-butoxycarbonyl-aminomethyl)-pyrrolidin-3-yl]-3-fluoro-phenyl}-carbamic Acid Benzyl Ester A solution of [4-{(3R,4S) and (3S,4R)-4-azidomethyl-1-benzyl-pyrolidin-3-yl}-3-fluoro-phenyl]-carbamic acid benzyl ester (10.3 mmol), 3.39 g triphenylphosphine (12.96 mmol) and 1.8 g H2O (MW: 18.0 100 mmol) in 80 ml THF was stirred at reflux for 22 hrs. The reaction was controlled by TLC. 2.25 ml triethylamine (16.2 mmol) and 2.82 g BOC$_2$O (12.9 mmol) were added and the mixture stirred at rt. The reaction was monitored by TLC. The solvent was evaporated and the residue was purified by chromatography, using an ethyl acetate/hexane 7/3 mixture as eluent.

Yield: 5.0 g, quantitative. MW: 533.64, (C31H36FN3O4) MS: 534.4 (M+H)+ Method ESI+.

{(3R,4S) and (3S,4R)-1-Benzyl-4-[2-fluoro-4-{(5R)-5-hydroxymethyl-2-oxo-oxazolidin-3-yl}-phenyl]-pyrrolidin-3-ylmethyl}-carbamic Acid Tert-Butyl Ester This compound was synthesized in analogy to the procedure described in Example 12 with 4.45 g {4-[(3R,4S) and (3S,4R)-1-benzyl-4 (tert-butoxycarbonylamino-methyl)-pyrrolidin-3-yl]-3-fluoro-phenyl}-carbamic acid benzyl ester (8.33 mmol).

Yield: 2.65 g, 63.6%. MW: 499.58, (C27H34FN3O5) MS: 500.4, (M+H)+ Method ESI+.

{(3R,4S) and (3S,4R)-1-Benzyl-4-[2-fluoro-4-{(5R)-5-hydroxymethyl-2-oxo-oxazolidin-3-yl}-phenyl]-pyrrolidin-3-ylmethyl}-carbamic Acid Tert-Butyl Ester This compound was synthesized in analogy to the procedure described in Example 12 with 2.60 g {(3R,4S) and (3S,4R)-1-benzyl-4-[2-fluoro-4-{(5R)-5-hydroxymethyl-2-oxo-oxazolidin-3-yl}-phenyl]-pyrrolidin-3-ylmethyl}-carbamic acid tert-butyl ester (5.20 mmol).

Yield: 2.70 g, quantitative. MW: 524.6, (C27H33FN6O4) MS: 525.6, (M+H)+ Method ESI+.

[(3R-4S) and (3S-4R)-4-{4-[(5S)-5-(Acetylamino-methyl)-2-oxo-oxazolidin-3-yl]-2-fluoro-phenyl}-1-benzyl-pyrrolidin-3-ylmethyl]-carbamic Acid Tert-Butyl Ester This compound was synthesized in analogy to the procedure described in Example 9 with 2.7 g {(3R,4S) and (3S,4R)-1-benzyl-4-[2-fluoro-4-{(5R)-5-hydroxymethyl-2-oxo-oxazolidin-3-yl}-phenyl]-pyrrolidin-3-ylmethyl}-carbamic acid tert-butyl ester (5.20 mmol).

Yield: 2.54 g, 90%. MW: 540.64, (C29H37FN4O5) MS: 541.3, (M+H)+ Method ESI+.

[(3R,4S) and (3S,4R)-4-{4-[(5S)-5-(Acetylamino-methyl)-2-oxo-oxazolidin-3-yl]-2-fluoro-phenyl}-pyrrolidin-3-ylmethyl]-carbamic Acid Tert-Butyl Ester This compound was synthesized in analogy to the procedure described in Example 12 with 2.5 g [(3R,4S) and (3S,4R)-4-{4-[(5S)-5-(acetylamino-methyl)-2-oxo-oxazolidin-3-yl]-2-fluoro-phenyl}-1-benzyl-pyrrolidin-3-ylmethyl]-carbamic acid tert-butyl ester (4.6 mmol).

Yield: 1.69 g, 81%. MW: 450.51, (C22H31FN4O5) MS: 451.5, (M+H)+ Method ESI+.

7-[(3R,4R) and (3S,4S)-3-{4-[(5S)-5-(Acetylamino-methyl)-2-oxo-oxazolidin-3-yl]-2-fluoro-phenyl}-4-aminomethyl-pyrrolidin-1-yl]-1-cyclopropyl-6-fluoro-4-oxo-1,4-dihydro-quinolin-3-carboxylic Acid A suspension of 130 mg 6,7-difluoro-1-cyclopropyl-4-oxo-1,4-dihydroquinoline-3-carboxylatoboron diacetate (MW: 393.11.0.33 mmol), 163 mg [(3R-4S) and (3S-4R)-4-{4-[(5S)-5-(acetylamino-methyl)-2-oxo-oxazolidin-3-yl]-2-fluoro-phenyl}-pyrrolidin-3-ylmethyl]-carbamic acid tert-butyl ester (0.36 mmol) and 56 mg DABCO (0.5 mmol) in 10 ml acetonitrile were heated under stirring with in microwave oven at 150° C. for 10 min. The reaction was monitored by TLC. The acetonitrile was evaporated, the residue dissolved in 3 ml methanol and treated with 3 ml 1.25 M HCl in methanol. The reaction was stirred for 20 h and purified by preparative HPLC.

Yield: 75 mg, 36%. MW: 595.61, (C30H31F2N5O6) MS: 596.5, (M+H)+ Method ESI+.

Example 14

7-{4-[2-(4-{4-[(5S)-5-(Acetylamino-methyl)-2-oxo-oxazolidin-3-yl]-2-fluoro-phenyl}-piperazin-1-yl)-2-oxo-ethyl]-piperazin-1-yl}-1-cyclopropyl-6-fluoro-4-oxo-1,4-dihydro-quinolone-3-carboxylic Acid

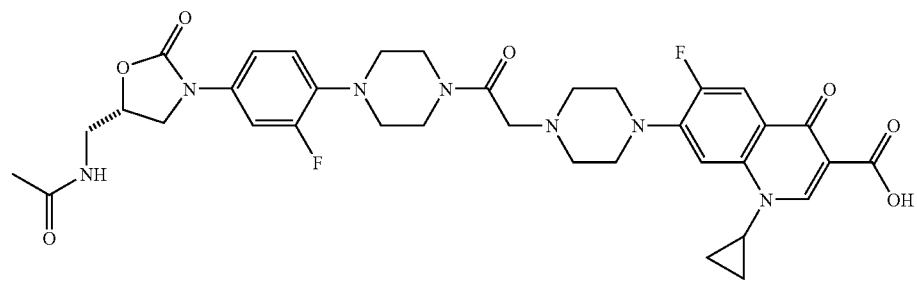

4-[2-(4-{4-[(5S)-5-(Acetylamino-methyl)-2-oxo-oxazolidin-3-yl]-2-fluoro-phenyl}-piperazin-1-yl)-2-oxo-ethyl]-piperazine-1-carboxylic Acid Tert-Butyl Ester To a stirred suspension of 672 mg of N-[(5S)-3-(3-fluoro-4-piperazine-1-yl-phenyl)-2-oxo-oxazolidin-5-ylmethyl]-acetamide (2 mmol) and 0.42 ml of triethylamine (3 mmol) in 30 ml dichloromethane was added at rt. a solution of 484 mg bromoacetylbromide (2.4 mmol) in 2 ml of dichloromethane. The reaction was monitored by TLC. The reaction solution was washed with water and brine, the dichloromethane layer dried over Mg sulfate, filtered and the filtrate evaporated to dryness. The residue was digested in 20 ml ether, the solid filtered and dried. The colorless solid was dissolved in 10 ml DMF, 372 mg N-Boc piperazine 2 mmol) and 276 mg of potassium carbonate (2 mmol) were added. The reaction was stirred over night at 60° C. and monitored by TLC. The DMF was evaporated to dryness, the residue purified by chromatography, using a 19/1 dichloromethane/methanol mixture as eluent.

Yield: 0.494 g, 44%. MW: 562.64, (C27H39FN6O6)
MS: 563.5 (M+H)$^+$, Method ESI$^+$

N-[(5S)-3-{3-Fluoro-4[4-(2-piperazin-1-yl-acetyl)-piperazin-1-yl]-phenyl}-2-oxo-oxazolidin-5-ylmethyl]-acetamide A solution of 0.490 g of 4-[2-(4-{4-[(5S)-5-(acetylamino-methyl)-2-oxo-oxazolidin-3-yl]-2-fluoro-phenyl}-piperazin-1-yl)-2-oxo-ethyl]-piperazine-1-carboxylic acid tert-butyl ester (0.87 mmol) in 2 ml dichloromethane was treated with 2 ml of TFA. The reaction was monitored by TLC. The solvent was evaporated and the residue dissolved in water. The water layer was neutralized with ammonium hydroxide and freeze-dried.

Yield: 0.494 g, 44%. MW: 462.52, (C22H31FN6O4)
MS: 463.6 (M+H)$^+$, Method ESI$^+$

7-{4-[2-(4-{4-[(5S)-5-(Acetylamino-methyl)-2-oxo-oxazolidin-3-yl]-2-fluoro-phenyl}-piperazin-1-yl)-2-oxo-ethyl]-piperazin-1-yl}-1-cyclopropyl-6-fluoro-4-oxo-1,4-dihydro-quinolone-3-carboxylic Acid A suspension of 169 mg 6,7-difluoro-1-cyclopropyl-4-oxo-1,4-dihydroquinoline-3-carboxylatoboron diacetate (0.33 mmol), 198 mg N-[(5S)-3-{3-fluoro-4[4-(2-piperazin-1-yl-acetyl)-piperazin-1-yl]-phenyl}-2-oxo-oxazolidin-5-ylmethyl]-acetamide (0.43 mmol), and 120 mg DABCO (1.07 mmol), in 10 ml acetonitrile was stirred at 150° C. in a micro wave oven for 10 min. The reaction was monitored by TLC. The acetonitrile was evaporated, the residue dissolved in 3 ml methanol and treated with 3 ml 1.25 M HCl in methanol. The reaction was stirred over night, and the solid filtered off. The solid was purified by prep HPLC.

Yield: 29 mg, 9.6%. MW: 707.74, (C35H39F2N7O7)
MS: 708.7, (M+H)$^+$, 706.6, (M−H)$^−$, Method ESI$^+$, ESI$^−$.

Example 15

7-(3-{4-[5(S)-5-(Acetylamino-methyl)-2-oxo-oxazolidin-3-yl]-2-fluoro-phenylamino}-azetidin-1-yl)-1-cyclopropyl-6-fluoro-4-oxo-1,4-dihydro-[1,8]naphthyridine-3-carboxylic Acid

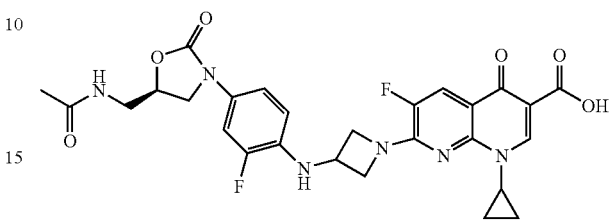

(1-Benzhydryl-azetidin-3-yl)-(2-fluoro-4-nitro-phenyl)-amine

A solution of 7.96 g of 1-benzhydrylazetidin-3-ylamine (33.41 mmol), 3.69 ml 3,4-difluoronitrobenzene (33.41 mmol) and 4.65 ml triethylamine (33.41 mmol)) in 50 ml ethyl acetate was stirred for 2 weeks at 60° C. The reaction was diluted with water and the product extracted with ethyl acetate. The organic layer was washed with water and brine, dried over MgSO4, filtered and evaporated.

Yield: 13.2 g, quantitative. MW: 393.46, (C23H24FN3O2)
1H-NMR (δ ppm DMSO-d$_6$): 2.78 (m, 2H, CH$_2$); 3.54 (m, 2H, CH$_2$); 4.02 (m, 1H, CH); 4.46 (s, 1H, CH); 6.69 (t, 1H, aro); 7.1-7.5 (m, 8H, biphenyl); 7.90 (m, 2H, aro)

3-[(Benzyloxycarbonyl-(4-benzyloxycarbonylamino-2-fluoro-phenyl)-amino]-azetidine-1-carboxylic Acid Benzyl Ester A suspension of 1 g of (1-benzhydryl-azetidin-3-yl)-(2-fluoro-4-nitro-phenyl)-amine (2.54 mmol) and 200 mg Pd/C 10% in 10 ml of a methanol with 5% acetic acid mixture was stirred under H$_2$ for 20 hrs. The Pd/C was filtered off and the filtrate evaporated. The oily residue was digested in hexane, and decanted in order to eliminate the hexane soluble biphenylmethane. MS 182 (M+H)$^+$, Method ESI$^+$. The remaining sticky oil was dissolved in 10 ml acetone. 10.0 ml of a saturated solution of sodium bicarbonate and 1.25 ml benzyl chloroformate (7.62 mmol) were added at 0° C. The mixture was stirred for 4 h at RT. The acetone was evaporated, and the residue diluted with ethyl acetate. The organic layer was washed with water and brine, dried over Mg sulfate, filtered and the filtrate evaporated. The residue was purified by chromatography using an ethyl acetate/hexane 4/5 mixture as eluent.

Yield: 916 mg, 63%. MW: 583.62, (C33H30FN3O6)
MS: 584.5 (M+H)$^+$, Method ESI$^+$.

3-{Benzyloxycarbonyl-[2-fluoro-4-{(5R)-5-hydroxymethyl-2-oxo-oxazolidin-3-yl}-phenyl]-amino}-azetidine-1-carboxylic Acid Benzyl Ester To a solution of 0.916 g of 3-(benzyloxycarbonyl-(4-benzyloxycarbonylamino-2-fluoro-phenyl)-amino]-azetidine-1-carboxylic acid benzyl ester (1.56 mmol) in 5 ml THF were added at −15° C. 0.767 ml of a 2.25M LDA (1.7 mmol) solution in THF. The mixture was allowed to warm up to 0° C.

and stirred for 5 min. Then, 0.26 ml of (R)-glycidyl butyrate (1.87 mmol) was added and the yellow solution was stirred for 2 h at RT. The reaction was quenched with a saturated solution of ammonium chloride. The mixture was diluted with ethyl acetate, the org. layer washed with water and brine and dried over Mg sulfate. The residue was purified by chromatography using a 95/5 dichloromethane/methanol mixture as eluent.

Yield: 377 mg, 43%. MW: 549.56, (C29H28FN3O7) MS: 550.7 (M+H)$^+$, Method ESI$^+$.

3-{[4-{(5R)-5-Azidomethyl-2-oxo-oxazolidin-3-yl}-2-fluoro-phenyl]-benzyloxycarbonyl-amino)-azetidine-1-carboxylic Acid Benzyl Ester To a solution of 1.08 g 3-{benzyloxycarbonyl-[2-fluoro-4-{(5R)-5-hydroxymethyl-2-oxo-oxazolidin-3-yl}-phenyl]-amino}-azetidine-1-carboxylic acid benzyl ester (2 mmol) in 20 ml dichloromethane was added at 0° C. 0.56 ml triethylamine (4 mmol) and 0.17 ml methanesulfonyl chloride (2.2 mmol). The reaction was stirred at RT for 1 hr and quenched with water. The organic layer was washed with brine, dried with Mg sulfate, filtered and the filtrate evaporated. Yield: 391 mg, 90%. Ms 584.0 (M+H)$^+$, Method ESI$^+$.

A suspension of the intermediate, 260 mg sodium azide (65.01, 4 mmol) and 37 mg tetrabutylammonium iodide (0.1 mmol) in 15 ml DMF was stirred at 80° C. for 16 h. The DMF was evaporated. The residue was diluted with water and ethyl acetate. The org. layer was washed with brine, dried over Mg sulfate, filtered and the filtrate evaporated.

Yield: 1.15 g, 93%. MW: 574.57, (C29H27FN6O6) MS: 575.4 (M+H)$^+$, Method ESI$^+$.

3-({4-[(5S)-5-(Acetylamino-methyl)-2-oxo-oxazolidin-3-yl]-2-fluoro-phenyl}-benzyloxycarbonyl-amino)-azetidine-1-carboxylic Acid Benzyl Ester A solution of 1.15 g 3-{[4-{(5R)-5-azidomethyl-2-oxo-oxazolidin-3-yl}-2-fluoro-phenyl]-benzyloxycarbonyl-amino)-azetidine-1-carboxylic acid benzyl ester (2 mmol), 0.36 ml water (20 mmol) and 0.277 g triphenylphosphine (2.2 mmol) was stirred for 16 h at 50° C. The solvent was evaporated. The residue was dissolved in 5 ml acetic acid and 2 ml acetic anhydride. The solution was stirred for 30 min and evaporated. The residue was purified by chromatography using a 9/1 ethyl acetate/methanol mixture as eluent.

Yield: 1.1 g, 93%. MW: 590.61, (C31H31FN4O7)

MS: 547.4 (M+H)$^+$, 546.5 (M−H)$^-$, Method ESI$^+$, Method ESI$^-$.

N-{(5S)-3-[4-(Azetidin-3-ylamino)-3-fluoro-phenyl]-2-oxo-oxazolidin-5-ylmethyl}-acetamide A suspension of 1.11 g of 3-({4-[(5S)-5-(acetylamino-methyl)-2-oxo-oxazolidin-3-yl]-2-fluoro-phenyl}-benzyloxycarbonyl-amino)-azetidine-1-carboxylic acid benzyl ester (1.88 mmol) and 200 mg Pd/c 10% in methanol was stirred under hydrogen for 5 h. The Pd/C was filtered and the filtrate evaporated to dryness.

Yield: 340 mg, 56%. MW: 322.34, (C15H19FN4O3); MS: 323.5 (M+H)$^+$, Method ESI$^+$.

7-(3-{4-[5(S)-5-(Acetylamino-methyl)-2-oxo-oxazolidin-3-yl]-2-fluoro-phenylamino}-azetidin-1-yl)-1-cyclopropyl-6-fluoro-4-oxo-1,4-dihydro-[1,8]naphthyridine-3-carboxylic Acid A solution of 85 mg of 7-chloro-1-cyclopropyl-6-fluoro-1,4-dihydro-4-oxo-1,8-naphthyridine-3-carboxylic acid 0.3 mmol), 97 mg N-{(5S)-3-[4-(azetidin-3-ylamino)-3-fluoro-phenyl]-2-oxo-oxazolidin-5-ylmethyl}-acetamide (0.3 mmol), 40 mg triethylamine (0.4 mmol) and 0.065 ml trimethylchlorosilane (0.6 mmol) in 2 ml DMSO was heated at 150° C. under stirring in a microwave oven for 10 min. The reaction was monitored by HPLC. The DMSO was evaporated, the residue digested in water, filtered and the solid purified by chromatography, using a 95/5 dichloromethane/methanol mixture as eluent.

Yield: 52 mg, 30%. MW: 568.54, (C27H26F2N6O6) MS: 569 (M+H)$^+$, Method ESI$^+$.

Known building block:

1-benzhydrylazetidin-3-ylamine, 40432-52-8, Beta Pharma Catalog

Example 16

7-[(3R)-3-{4-[(5S)-5-(Acetylamino-methyl)-2-oxo-oxazolidin-3-yl]-2-fluoro-phenylamino}-pyrrolidin-1-yl]-1-cyclopropyl-6-fluoro-4-oxo-1,4-dihydro-[1,8]-naphthyridine-3-carboxylic Acid

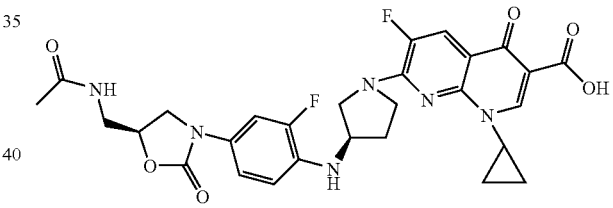

7-[(3R)-3-{4-[(S)-5-(Acetylamino-methyl)-2-oxo-oxazolidin-3-yl]-2-fluoro-phenylamino}-pyrrolidin-1-yl]-1-cyclopropyl-6-fluoro-4-oxo-1,4-dihydro-[1,8]naphthyridine-3-carboxylic Acid A suspension of 119 mg N-{(5S)-3-[3-fluoro-4-(pyrrolidin-3-ylamino)-phenyl]-2-oxo-oxazolidin-5-ylmethyl}-acetamide (0.35 mmol), 100 mg 7-chloro-1-cyclopropyl-6-fluoro-1,4-dihydro-4-oxo-1,8-naphthyridine-3-carboxylic acid, 148 μl triethylamine (1.05 mmol) and 89 μl trimethylchlorosilane (0.70 mmol) in 2 ml DMSO was stirred in a microwave oven at 150° C. for 10 min. The DMSO was evaporated, the residue digested in water and the solid filtrated. The solid was purified by chromatography using a 95/5 dichloromethane/methanol mixture.

Yield: 10 mg, 5%. MW: 582.56, (C28H28F2N6O6) MS: 583.2 (M+H)$^+$, Method ESI$^+$.

Known building blocks:

7-chloro-1-cyclopropyl-6-fluoro-1,4-dihydro-4-oxo-1,8-Naphthyridine-3-carboxylic acid: CAS 100361-18-0, Louston International.

Example 17

7-[(3R,4S) and (3S,4R)-3-(-4{4-[(5S)-5-(Acetylamino-methyl)-2-oxo-oxazolidin-3-yl]-2-fluoro-phenyl}piperazine-1-carbonyl)-4-aminomethyl-pyrrolidin-1-yl]-1-cyclopropyl-6-fluoro-4-oxo-1,4-dihydro-quinoline Carboxylic Acid

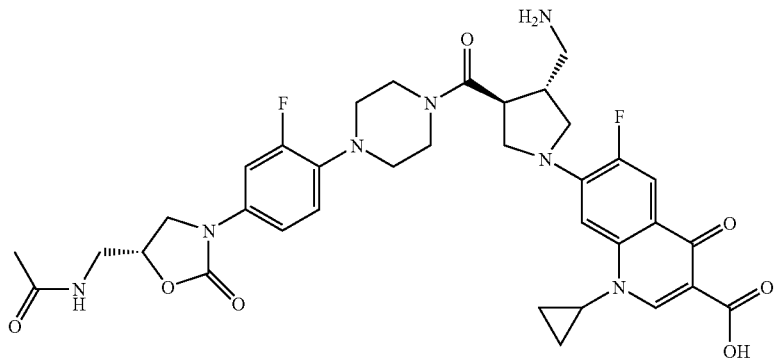

(3R,4R) and (3S,4S)-1-Benzyl-4-(tert-butoxycarbonylamino-methyl)-pyrrolidine-3-carboxylic Acid Ethyl Ester To a solution of 2 g of 4-tert-butoxycarbonylamino-but-2-enoic acid ethyl ester (8.72 mmol) and 5.12 g N-[(pentyloxy)methyl]-N-[(trimethylsilyl)methyl]-benzene-methanamine (17.4 mmol) in 50 ml dichloromethane was added 10 micro-l. trifluoroacetic acid. The reaction was monitored by TLC. The reaction was complete after 10 min. The mixture was diluted with dichloromethane, washed with sat. sodium bicarbonate solution and brine, dried over Mg sulfate, filtered and the filtrate evaporated. The residue was purified by filtration over a short silica column, using a 7/3 hexane/ethyl acetate mixture as eluent.

Yield: 2.96 g, 93%. MW: 362.47, (C20H30N2O4) MS: 363.6 (M+H)$^+$, Method ESI$^+$.

(3R,4R) and (3S,4S)-1-Benzyl-4-(tert-butoxycarbonylamino-methyl)-pyrrolidine-3-carboxylic Acid To a solution of 2.9 (3R,4R) and (3S,4S)-1-benzyl-4-(tert-butoxycarbonylamino-methyl)-pyrrolidine-3-carboxylic acid ethyl ester (8.0 mmol) in 50 ml THF were added 671 mg lithium hydroxide mono hydrate (16 mmol) and 0.5 ml water. The solution was stirred at 40° C. and the reaction monitored by TLC. After 72 h the solvent was evaporated, the residue dissolved in dichloromethane, washed with water and brine, dried over Mg sulfate, filtered and evaporated. The residue was crystallized from a dichloromethane/hexane mixture.

Yield: 1.9 g, 71%. MW: 334.41, (C18H26N2O4) MS: 335.3 (M+H)$^+$, 333.3 (M−H)$^−$, Method ESI$^+$, ESI$^−$.

[(3R,4R) and (3S,4S)-4-(4-{4-[(5S)-5-(Acetylamino-methyl)-2-oxo-oxazolidin-3-yl]-2-fluoro-phenyl}-piperazine-1-carbonyl)-1-benzyl-pyrrolidin-3-ylmethyl]-carbamic Acid Tert-Butyl Ester To solution of 0.668 g of 1-benzyl-4-(tert-butoxycarbonyl-amino-methyl)-pyrrolidine-3-carboxylic acid (2 mmol), 0.6 ml triethylamine (4 mmol), and 0.662 g N-[{(5S)-3[3-fluoro-4-(1-piperazinyl)phenyl]-2-oxo-5-oxazolidinyl}methyl]-acetamide (2 mmol) in 50 ml dry DMF was added 0.796 g of O-(benzotriazol-1-yl)-N,N,N',N'-tetramethyluronium-hexafluorophosphate (252.1 mmol). The reaction was stirred at rt. for 20 hrs. The DMF was evaporated, the residue dissolved in ethyl acetate, washed with water and brine, dried over Mg sulfate, filtered and the filtrate evaporated. The residue was purified by chromatography, using a 9/1 dichloromethane/methanol mixture as eluent.

Yield: 1.14 g, 87%. MW: 652.77, (C34H45FN6O6) MS: 653.7 (M+H)$^+$, Method ESI$^+$.

[[(3R,4R) and (3S,4S)-4-(4-{4-[(5S)-5-(Acetylamino-methyl)-2-oxo-oxazolidin-3-yl]-2-fluoro-phenyl}-piperazine-1-carbonyl)-pyrrolidin-3-ylmethyl]-carbamic Acid Tert-Butyl Ester A suspension of 1.1 g [(3R,4R) and (3S,4S)-4-(4-{4-[(5S)-5-(acetylamino-methyl)-2-oxo-oxazolidin-3-yl]-2-fluoro-phenyl}-piperazine-1-carbonyl)-1-benzyl-pyrrolidin-3-ylmethyl]-carbamic acid tert-butyl ester (1.68 mmol) and 0.2 g Pd/C 10% in 10 ml methanol and 2 ml acetic acid was stirred under hydrogen. The reaction was monitored by TLC. The solvent was evaporated to leave an amorphous solid.

Yield: 1.14 g, 87%. MW: 562.64, (C27H39FN6O6) MS: 563.3, (M+H)$^+$, Method ESI$^+$.

7-[(3R,4S) and (3S,4R)-3-(-4{4-[(5S)-5-(Acetylamino-methyl)-2-oxo-oxazolidin-3-yl]-2-fluoro-phenyl}piperazine-1-carbonyl)-4-aminomethyl-pyrrolidin-1-yl]-1-cyclopropyl-6-fluoro-4-oxo-1,4-dihydro-quinoline Carboxylic Acid A solution of 141 mg [[(3R,4R) and (3S,4S)-4-(4-{4-[(5S)-5-(acetylamino-methyl)-2-oxo-oxazolidin-3-yl]-2-fluoro-phenyl}-piperazine-1-carbonyl)-pyrrolidin-3-ylmethyl]-carbamic acid tert-butyl ester (0.25 mmol), 102 mg 7-chloro-6-fluoro-1-cyclopropyl-4-oxo-1,4-dihydro-quinoline-3-carboxylatoboron diacetate (0.25 mmol) and 61 mg DABCO (0.5 mmol) in 2 ml DMSO was stirred at 150° C. for 12 min in a microwave oven. The reaction was monitored by TLC. The DMSO was evaporated, the residue dissolved in acetonitrile, diluted with water and concentrated. The solid was filtered and purified by prep HPLC.

Yield: 20 mg, 11.3%. MW: 707.74, (C35H39F2N7O7) MS: 708.7, (M+H)$^+$, Method ESI$^+$.

Example 18

7-[(3R,4S) and (3S,4R)-3-(4-{4-[(5S)-5-(Acetylamino-methyl)-2-oxo-oxazolidin-3-yl]-2-fluorophenyl}-piperazine-1-carbonyl)-4-aminomethyl-pyrrolidin-1-yl)1-cyclopropyl-6-fluoro-4-oxo-1,4-dihydro-[1,8]naphthyridine-3-carboxylic Acid

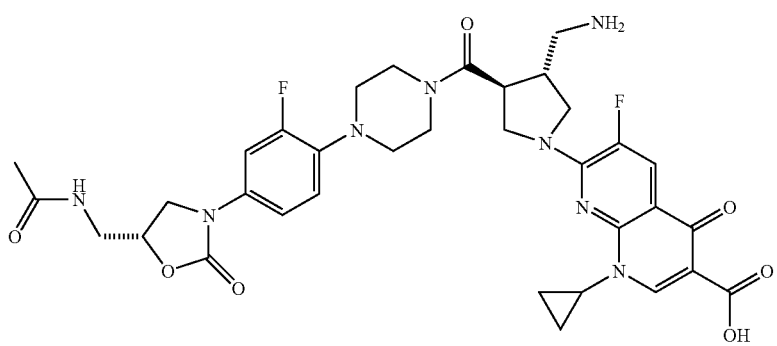

7-[(3R,4S) and (3S,4R)-3-(4-{4-[(5S)-5-(Acetylamino-methyl)-2-oxo-oxazolidin-3-yl]-2-fluorophenyl}-piperazine-1-carbonyl)-4-aminomethyl-pyrrolidin-1-yl)1-cyclopropyl-6-fluoro-4-oxo-1,4-dihydro-[1,8]naphthyridine-3-carboxylic Acid A solution of 99 mg 7-chloro-1-cyclopropyl-6-fluoro-1,4-dihydro-4-oxo-[1,8]naphthyridine-3-carboxylic acid (0.35 mmol), 197 mg [(3R,4R) and (3S,4S)-4-(4-{4-[5-(acetylamino-methyl)-2-oxo-oxazolidin-3-yl]-2-fluoro-phenyl}-piperazine-1-carbonyl)-pyrrolidin-3-ylmethyl]-carbamic acid tert-butyl ester (0.35 mmol), 146 microL triethylamine (1.05 mmol) and 76 mg trimethylchlorsilane (0.70 mmol) were dissolved in 2 ml DMSO. The solution was heated at 150° C. under stirring in a microwave oven for 10 min. The reaction was monitored by TLC. The DMSO was evaporated, the residue digested in water, filtered and the solid purified by chromatography, using dichloromethane/methanol mixture as eluent. The intermediate was crystallized from acetonitrile. The crystals were dissolved in a 1.25 M HCl and stirred at rt. The reaction was monitored by TLC. The methanol was evaporated and the residue purified by preparative HPLC.

Yield: 130 mg, 52%. MW: 708.72, (C34H38F2N8O7) MS: 709.6, (M+H)+, Method ESI+.

Example 19

7-(4-{5-[(5S)-5-(Acetylamino-methyl)-2-oxo-oxazolidin-3-yl]-pyridin-2-yl}-1-piperazin-1-yl)-1-cyclopropyl-6-fluoro-4-oxo-1,4-dihydro-[1,8]naphthyridine-3-carboxylic Acid

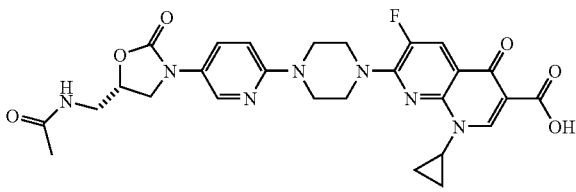

4-(Benzyloxycarbonylamino-pyridin-2-yl)-piperazine-1-carboxylic Acid Tert-Butyl Ester To a solution of 4 g 4-(5-nitro-pyridin-2-yl)-piperazine-1-carboxylic acid tert-butyl ester (12.9 mmol) in 50 ml ethyl acetate and 50 ml methanol was added 0.5 g Pd/C 10%. The suspension was stirred under a hydrogen atmosphere. The reaction was monitored by TLC. The Pd/C was filtered, the filtrate evaporated to dryness, the residue dissolved in 150 ml acetone, diluted with 75 ml of a saturated solution of sodium bicarbonate, and reacted with 2.65 g of benzyl chloroformate (15.56 mmol). The reaction was monitored by TLC. The acetone was evaporated, the residue dissolved in ethyl acetate, the org. layer washed with water and brine, dried over Mg sulfate, filtered and the filtrate evaporated to dryness. The residue was crystallized from an ethyl acetate/hexane mixture.

Yield: 4.79 g, 89%. MW: 412.49, (C22H28N4O4) MS: 413.4, (M+H)+, Method ESI+.

4-[(5R)-5-(Hydroxymethyl-2-oxo-oxazolidin-3-yl)-pyridin-2-yl]-piperazine-1-carboxylic Acid Tert-Butyl Ester To a stirred solution of 4.69 g 4-(benzyloxycarbonylamino-pyridin-2-yl)-piperazine-1-carboxylic acid tert-butyl ester (11.37 mmol) in 50 ml of THF at −70 C was added 7.46 ml of a 1.6M n-BuLi solution in N-hexane (11.93 mmol). The mixture was stirred at 0 C for 15 min, and 2.06 ml of R(−)-glycidyl butyrate (14.7 mmol) was added. The reaction was monitored by TLC. The reaction was then quenched with a saturated solution of ammonium chloride, diluted with ethyl acetate and washed with water and brine. The org. layer was dried over Mg sulfate, filtered and the filtrate evaporated to dryness. The residue was purified by chromatography, using an ethyl acetate/dichloromethane 9/1 mixture as eluent.

Yield: 2.58 g, 60%. MW: 378.43, (C18H26N4O5) MS: 379.6 (M+H)$^+$, Method ESI$^+$.

4-[(5R)-5-(Azidomethyl-2-oxo-oxazolidin-3-yl)-pyridin-2-yl]piperazine-1-carboxylic Acid Tert-Butyl Ester This compound was synthesized in analogy to the procedure described in Example 12 using 2.5 g 4-[(5R)-5-(hydroxymethyl-2-oxo-oxazolidin-3-yl)-pyridin-2-yl]-piperazine-1-carboxylic acid tert-butyl ester (6.62 mmol).

Yield: 2.3 g, 86%. MW: 403.44, (C18H25N7O4) MS: 404.4, (M+H)$^+$, Method ESI$^+$.

4-{5-[(5S)-5-(Acetylamino-methyl)-2-oxo-oxazolidin-3-yl]-pyridin-2-yl}-piperazine-1-carboxylic Acid Tert-Butyl Ester A suspension of 2.25 g of 4-[(5R)-5-(azidomethyl-2-oxo-oxazolidin-3-yl)-pyridin-2-yl]piperazine-1-carboxylic acid tert-butyl ester (6.62 mmol), and Pd/C 10% in methanol was stirred under hydrogen. The reaction was monitored by TLC. The solvent was evaporated and the residue dissolved in 10 ml acetic acid. 2 ml of acetic anhydride were added to the solution and the reaction monitored by TLC. The solvent was evaporated and the residue purified by chromatography, using a dichloromethane/methanol 9/1 mixture as eluent.

Yield: 0.572 g, 24%. MW: 419.48, (C20H29N5O5) MS: 420.4, (M+H)$^+$, Method ESI$^+$.

N-[(5S)-2-oxo-3-(6-piperazin-1-yl-pyridin-3-yl)-oxazolidin-5-ylmethyl]-acetamide 0.54 g of 4-{5-[(5S)-5-(acetylamino-methyl)-2-oxo-oxazolidin-3-yl]-pyridin-2-yl}-piperazine-1-carboxylic acid tert-butyl ester (1.28 mmol) was dissolved in a 1.25 M HCl solution in methanol. The solution was stirred and the reaction monitored by TLC. The methanol was evaporated, the residue dissolved in water, neutralized with sodium bicarbonate and the water evaporated to dryness. The residue was digested in a 9/1 dichloromethane/methanol. The insoluble salt was filtered off, the filtrate evaporated to dryness to leave a pale brown solid.

Yield: 0.381 g, 93%. MW: 3198.36, (C15H21N5O3) MS: 320.1, (M+H)$^+$, Method ESI$^+$.

7-(4-{5-[(5S)-5-(Acetylamino-methyl)-2-oxo-oxazolidin-3-yl]-pyridin-2-yl}-1-piperazin-1-yl)-1-cyclopropyl-6-fluoro-4-oxo-1,4-dihydro-[1,8]naphthyridine-3-carboxylic Acid This compound was synthesized in analogy to the procedure described in Example 10 using 0.135 g N-[2-oxo-3-(6-piperazin-1-yl-pyridin-3-yl)-oxazolidin-5-ylmethyl]-acetamide (0.42 mmol) and 120 mg 7-chloro-1-cyclopropyl-6-fluoro-1,4-dihydro-4-oxo-[1,8]naphthyridine-3-carboxylic acid (0.42 mmol).

Yield: 0.113 g, 47%. MW: 565.57, (C27H28FN7O6) MS: 566.8, (M+H)$^+$; 564.8, (M−H)$^−$, Method ESI$^+$, ESI$^−$.

Example 20

7-(4-{5-[(5S)-5-(Acetylamino-methyl)-2-oxo-oxazolidin-3-yl]-pyridin-2-yl}-piperazin-1-yl)-1-cyclopropyl-6-fluoro-4-oxo-1,4-dihydro-quinoline-3-carboxylic Acid

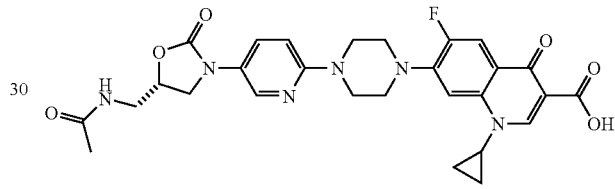

A solution of 127 mg (S)—N-[2-oxo-3-(6-piperazin-1-yl-pyridin-3-yl)-oxazolidin-5-ylmethyl]-acetamide (0.4 mmol), 163 mg 7-chloro-6-fluoro-1-cyclopropyl-4-oxo-1,4-dihydro-quinoline-3-carboxylatoboron diacetate (0.4 mmol) and 90 mg DABCO in 2 ml DMSO was stirred at 150° C. for 12 min. in a microwave oven. The reaction was monitored by TLC. The DMSO was evaporated, the residue digested in water. The solid was filtered and purified by chromatography, using dichloromethane/methanol as eluent.

Yield: 0.027 g, 11.9%. MW: 564.58, (C28H29FN6O6) MS: 565.8 (M+H)$^+$, 563.6 (M−H)$^−$, Method ESI$^+$, ESI$^−$.

Example 21

7-[(3R)-3-(4-{4[(5S)-5-(Acetylamino-methyl)-2-oxo-oxazolidin-3-yl]-2-fluoro-phenyl}-piperazin-1-yl)-pyrrolidin-1-yl]-1-cyclopropyl-6-fluoro-4-oxo-1,4-dihydro-[1,8]naphthyridine-3-carboxylic Acid

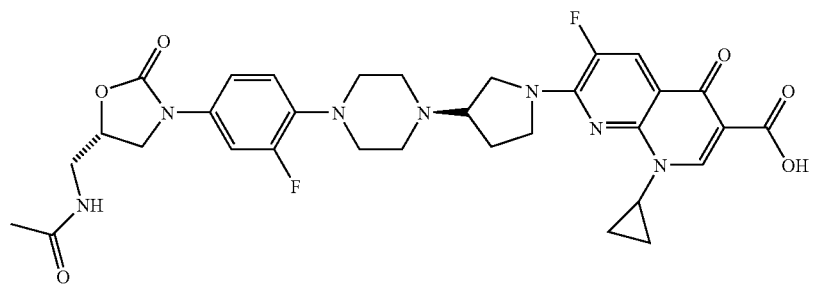

(3R)-3-[4-(2-Fluoro-4-nitro-phenyl)-piperazin-1-yl]-pyrrolidine-1-carboxylic Acid Allyl Ester This compound was synthesized in analogy to the procedure described in Example 12 using (3R)-3-amino-pyrrolidine-1-carboxylic acid allyl ester (1.28 mmol) and 2,2-[(2-fluoro-4-nitrophenyl)imino]bis-ethanol (40.5 mmol).

Yield: 3.38 g, 32%. MW: 378.40, (C18H23FN4O4) MS: 379.5, (M+H)$^+$, Method ESI$^+$.

(3R)-3-[4-(2-Fluoro-4-nitro-phenyl)-piperazin-1-yl]-pyrrolidine-1-carboxylic Acid Tert-Butyl Ester To a solution of 3.33 g (3R)-3-[4-(2-fluoro-4-nitro-phenyl) piperazin-1-yl]pyrrolidine-1-carboxylic acid allyl ester (8.8 mmol) in 60 ml THF were added 130 mg of bis (triphenylphosphine)-palladium(II) dichloride (0.088 mmol), 1.0 ml acetic acid (17.6 mmol), and 4.66 ml tributyl tinnhydride (17.6 mmol). The reaction was stirred at rt for 1 h and monitored by TLC. The suspension was diluted with 100 ml ether and a pale yellow solid precipitated. The solid was filtered, washed with ether and hexane and dried. The solid was diluted with 100 ml dichloromethane, 2.30 g BOC anhydride (MW: 218.25, 17.6 mmol) was added and the reaction stirred at RT over night and monitored by TLC. The reaction was diluted with dichloromethane, the org. layer washed with water and brine dried over Mg sulfate and filtered. The filtrate was evaporated. The residue was purified by chromatography, using ethyl acetate as eluent.

Yield: 0.740 g, 21%. MW: 394.44, (C19H27FN4O4) MS: 395.3, (M+H)$^+$, Method ESI$^+$.

(3R)-3-[4-(4-Benzyloxycarbonylamino-Fluoro-phenyl)-piperazin-1-yl]-pyrrolidine-1-carboxylic Acid Tert-Butyl Ester This compound was synthesized in analogy to the procedure described in Example 19 using 0.780 g (3R)-3-[4-(2-fluoro-4-nitro-phenyl)-piperazin-1-yl]-pyrrolidine-1-carboxylic acid tert-butyl ester (1.97 mmol).

Yield: 0.768 g, 78%. MW: 498.6, (C27H35FN4O4) MS: 499.7, (M+H)$^+$, Method ESI$^+$.

(3R)-3-{4-[2-Fluoro-4-{(5R)-5-hydroxymethyl-2-oxo-oxazolidin-3-yl}-phenyl]-piperazin-1-yl}-pyrrolidine-1-carboxylic Acid Tert-Butyl Ester This compound was synthesized in analogy to the procedure described in Example 19 using 0.780 g (3R)-3-[4-(4-benzyloxycarbonylamino-fluoro-phenyl)-piperazin-1-yl]-pyrrolidine-1-carboxylic acid tert-butyl ester (1.54 mmol).

Yield: 0.475 g, 66%. MW: 464.54, (C23H33FN4O5) MS: 465.4, (M+H)$^+$, Method ESI$^+$.

(3R)-3-{4-[4-{(5R)-5-Azidomethyl-2-oxo-oxazolidin-3-yl}-2-fluoro-phenyl]-piperazin-1-yl}-pyrrolidine-1-carboxylic Acid Tert-Butyl Ester This compound was synthesized in analogy to the procedure described in Example 19 using 0.475 g (3R)-3-{4-[2-fluoro-4-{(5R)-5-hydroxymethyl-2-oxo-oxazolidin-3-yl}-phenyl]-piperazin-1-yl}-pyrrolidine-1-carboxylic acid tert-butyl ester (1.02 mmol).

Yield: 0.500 g, quantitative. MW: 489.55, (C23H32FN7O4) MS: 490.4, (M+H)$^+$, Method ESI$^+$.

(3R)-3-{4-[4-{(5S)-5-Acetylaminomethyl-2-oxo-oxazolidin-3-yl}2-fluoro-phenyl]-piperazin-1-yl}-pyrrolidine-1-carboxylic Acid Tert-Butyl Ester This compound was synthesized in analogy to the procedure described in Example 19 using 0.475 g (3R)-3-{4-[4-{(5R)-5-azidomethyl-2-oxo-oxazolidin-3-yl}2-fluoro-phenyl]-piperazin-1-yl}-pyrrolidine-1-carboxylic acid tert-butyl ester (1.02 mmol).

Yield: 0.398 g, 77%. MW: 505.59, (C25H36FN5O5) MS: 506.4, (M+H)$^+$, Method ESI$^+$.

N-{(5S)-3-[3-Fluoro-4-(4-{(3R)-pyrrolidin-3-yl}-piperazin-1-yl)-phenyl]-2-oxo-oxazolidin-5-ylmethyl}-acetamide This compound was synthesized in analogy to the procedure described in Example 19 using 0.398 g (3R)-3-{4-[4-{(5S)-5-acetylaminomethyl-2-oxo-oxazolidin-3-yl}2-fluoro-phenyl]-piperazin-1-yl}-pyrrolidine-1-carboxylic acid tert-butyl ester (0.79 mmol).

Yield: 0.398 g, 77%. MW: 405.47, (C20H28FN5O3) MS: 406.8, (M+H)$^+$, Method ESI$^+$.

7-[(3R)-3-(4-{4[(5S)-5-(Acetylamino-methyl)-2-oxo-oxazolidin-3-yl]-2-fluoro-phenyl}-piperazin-1-yl)-pyrrolidin-1-yl]-1-cyclopropyl-6-fluoro-4-oxo-1,4-dihydro-[1,8]naphthyridine-3-carboxylic Acid This compound was synthesized in analogy to the procedure described in Example 19 using 0.0 90 g N-{(5S)-3-[3-fluoro-4-(4-{(3R)-pyrrolidin-3-yl}-piperazin-1-yl)-phenyl]-2-oxo-oxazolidin-5-ylmethyl}-acetamide (0.22 mmol) and 7-chloro-1-cyclopropyl-6-fluoro-1,4-dihydro-4-oxo-[1,8]naphthyridine-3-carboxylic acid (0.22 mmol).

Yield: 47 mg, 32%. MW: 651.68, (C32H35F2N7O6) MS: 652.5, (M+H)$^+$; 650.8, (M−H)$^−$, Method ESI$^+$, ESI$^−$.

Example 22

1-Cyclopropyl-6-fluoro-7-(4-{2-fluoro-4-[(5R)-5-(methansulfonylamino-methyl)-2-oxo-oxazolidin-3-yl]-phenyl}-piperazin-1-yl)-4-oxo-1,4-dihydro-[1,8]naphthyridine-3-carboxylic Acid

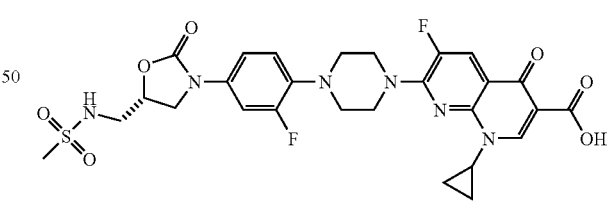

4-{2-Fluoro-4-[(5R)-5-(methansulfonylamino-methyl)-2-oxo-oxazolidin-3-yl]-phenyl}-piperazin-1-carboxylic Acid Tert-Butyl Ester This compound was synthesized in analogy to the procedure described in Example 9 using 4-[4-{(5S)-5-aminomethyl-2-oxo-oxazolidin-3-yl}-2-fluoro-phenyl]-piperazine-1-carboxylic acid tert-butyl ester (1.5 mmol).

Yield: 0.505 g, 71%. MW: 472.53, (C20H29FN4O6S) MS: 473.4, (M+H)$^+$; 471.7, (M−H)$^−$, Method ESI$^+$, ESI$^−$.

N-[(5R)-3-(3-Fluoro-4-piperazin-1-yl-phenyl)-2-oxo-oxazolidin-5-ylmethyl]-methansulfonamide This compound was synthesized in analogy to the procedure described in Example 19 using 0.5 g 4-{2-fluoro-4-[(5R)-5-(methansulfonylamino-methyl)-2-oxo-oxazolidin-3-yl]-phenyl}-piperazin-1-carboxylic acid tert-butyl ester (1.06 mmol).

Yield: 0.39 g, quantitative. MW: 372.42, (C15H21FN4O4S) MS: 373.0, (M+H), Method ESI+.

1-Cyclopropyl-6-fluoro-7-(4-{2-fluoro-4-[(5R)-5-(methan-sulfonylamino-methyl)-2-oxo-oxazolidin-3-yl]-phenyl}-piperazin-1-yl)-4-oxo-1,4-dihydro-[1,8]naphthyridine-3-carboxylic Acid This compound was synthesized in analogy to the procedure described in Example 10 using 0.082 g N-[(5R)-3-(3-fluoro-4-piperazin-1-yl-phenyl)-2-oxo-oxazolidin-5-ylmethyl]-methansulfonamide (0.22 mmol) and 0.067 g 7-chloro-1-cyclopropyl-6-fluoro-1,4-dihydro-4-oxo-[1,8]naphthyridine-3-carboxylic acid (0.22 mmol).

Yield: 0.079 g, 58%. MW: 618.62, (C27H28F2N6O7S) MS: 619.8, (M+H)+; 617.7, (M−H)−, Method ESI+, ESI−.

Example 23

7-(4-{4-[(5S)-5-(Acetylamino-methyl)-2-oxo-oxazolidin-3-yl]-2-fluoro-phenylamino}-piperidin-1-yl)-1-cyclopropyl-6-fluoro-4-oxo-1,4-dihydro-[1,8]naphthyridine-3-carboxylic Acid

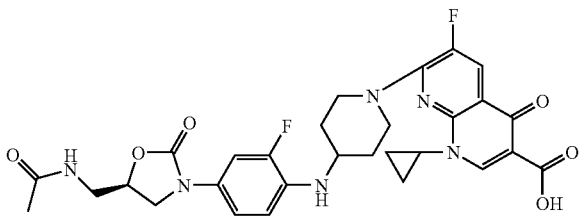

(1-Benzyl-piperidin-4-yl)-(2-fluoro-4-nitro-phenyl)-amine 9.54 g (MW: 159.09, 60 mmol) 3,4-difluorobenzene, 11.4 g (60 mmol) 4-amino-N-benzylpiperidine and 9.1 66 mmol) triethylamine in acetonitrile were stirred at reflux for 16 h. The solution was diluted with EtOAc, washed with water, and brine, dried over MgSO4 and filtrated. The filtrate was evaporated, and the crystals were recrystallized with an ETOAc/hexane mixture.

Yield: 13.5 g, 70%. MW: 329.37, (C18H20FN3O2) MS: 430.1(M+H)+, Method ESI+.

2-Fluoro-N'-piperidin-4-yl-benzene-1,4-diamine

A mixture of 5 g (15 mmol) of (1-benzyl-piperidin-4-yl)-(2-fluoro-4-nitro-phenyl)-amine in MeOH/EtOAc with Pd/C 10% was stirred under H2 at RT. The reaction was monitored by TLC. The Pd/C was filtered and the filtrate evaporated to dryness.

Yield: 3.2 g, quant. MW: 209.26, (C11H16FN3) MS: 210.3 (M+H)+, Method ESI+.

4-(4-Benzyloxycarbonylamino-2-fluoro-phenylamino)-piperidine-1-carboxylic Acid Benzyl Ester To a mixture of 3.2 g (15 mmol) 2-fluoro-N'-piperidin-4-yl-benzene-1,4-diamine in 150 ml acetone, was added 75 ml of sat NaHCO3, and 5.3 ml (37.5 mmol) benzyl chloroformate. It was stirred for 2 h, the acetone was evaporated, and the water layer extracted twice with EtOAc. The organic layer was washed with water and brine, dried over MgSO4, filtered and the filtrate evaporated. The residue was purified by chromatography using a hex/EtOAc 1:1 mixture.

Yield: 1.5 g, quant. MW: 477.54, (C27H28FN3O4) MS: 478.4 (M+H)+, Method ESI+.

4-[2-Fluoro-4-{(5R)-5-hydroxymethyl-2-oxo-oxazolidin-3-yl}-phenylamino]-piperidine-1-carboxylic Acid Benzyl Ester To a solution of 6.6 g (15 mmol) 4-(4-benzyloxycarbonylamino-2-fluoro-phenylamino)-piperidine-1-carboxylic acid benzyl ester in 50 ml THF at −78° C. was added dropwise 12.12 ml nBuli 1.6 M (19.5 mmol). The mixture was further stirred at this temperature for 10 min. The resulting yellow solution was allowed to reach −40° C. over 10 min. 3.0 ml (21 mmol) of (R)-glycidyl butyrate was then added and the solution was allowed to reach slowly RT and further stirred for 16 h. The reaction was quenched with a saturated ammonium chloride solution, diluted with 400 ml of EtOAc. The organic layer was washed with water and brine, dried over MgSO4, filtered and evaporated to dryness. The residue was purified by chromatography using a CH2Cl2/MeOH 5% mixture.

Yield: 2.58 g, 50%. MW: 443.47, (C23H26FN3O5) MS: 444.6 (M+H)+, Method ESI+.

4-[4-{(5R)-5-Azidomethyl2-oxo-oxazolidin-3-yl}-2-fluoro-phenylamino]-piperidine-1-carboxylic Acid Benzyl Ester To a solution of 2.5 g of 4-[2-fluoro-4-{(5R)-5-hydroxymethyl-2-oxo-oxazolidin-3-yl}-phenylamino]-piperidine-1-carboxylic acid benzyl ester (5.6 mmol) and 1.57 ml (11.2 mmol) triethylamine in 60 ml dichloromethane, was added at 0° C. 0.48 ml methanesulfonyl chloride (6.16 mmol). The reaction mixture was allowed to warm up to rt and further stirred for 30 min. The reaction was quenched with water, the organic layer washed with water and brine, dried over Mg sulfate, filtered and the filtrate evaporated.

Yield: 2.88 g, 98%. Ms 522.3 (M+H)+, Method ESI+.

A suspension of the residue, 717 mg sodium azide (11.04 mmol) and 100 mg tetrabutylammonium iodide (0.27 mmol) in 10 ml DMF was stirred at 80° C. for 20 hrs. The DMF was evaporated, the residue dissolved in ethyl acetate, washed with water and brine, the org. layer dried over Mg sulfate, filtered and the filtrate evaporated to dryness.

Yield: 2.5 g, 97%. MW: 468.49, (C23H25FN6O4) MS: 469.7(M+H)+, Method ESI+.

4-[4-{(5S)-5-Aminomethyl-2-oxo-oxazolidin-3-yl}-2-fluoro-phenylamino]-piperidine-1-carboxylic Acid Benzyl Ester A solution of 2.51 g (5.35 mmol) 4-[4-{(5R)-5-azidomethyl2-oxo-oxazolidin-3-yl}-2-fluoro-phenylamino]-piperidine-1-carboxylic acid benzyl ester, 1.54 g (5.88 mmol) triphenylphosphine and 964 µl (53.5 mmol) water in 30 ml THF was stirred at 50° C. for 16 h.

The THF was evaporated. The residue was purified by chromatography using a dichloromethane/methanol 9/1 mixture with 1% ammonia.

Yield: 1.44 g, 78%. MW: 442.49, (C23H27FN4O4) MS: 443.6 (M+H)+, Method ESI+.

4-{4-[(5S)-5-(Acetylamino-methyl)-2-oxo-oxazolidin-3-yl]-2-fluoro-phenylamino}-piperidine-1-carboxylic Acid Benzyl Ester A solution of 450 mg 4-[4-{(5S)-5-aminomethyl-2-oxo-oxazolidin-3-yl}-2-fluoro-phenylamino]-piperidine-1-carboxylic acid benzyl ester (1.01 mmol), 2 ml acetic acid and 0.093 ml (1 mmol) acetic anhydride was stirred at RT for 1 h. The solvents were evaporated.

Yield: 484 mg, quant. MW: 484.53, (C25H29FN4O5) MS: 485.7 (M+H)+, Method ESI+.

N-{(5S)-3-[3-Fluoro-4-(piperidin 4-ylamino)-phenyl]-2-oxo-oxazolidin-5-yl methyl}-acetamide A suspension of 480 mg (1 mmol) 4-{4-[(5S)-5-(acetylamino-methyl)-2-oxo-oxazolidin-3-yl]-2-fluoro-phenylamino}-piperidine-1-carboxylic acid benzyl ester and Pd/C in 2 ml of a methanol/acetic acid 1/1 mixture was stirred under H2 for 4 h. The Pd/C was filtered and the filtrate was evaporated to dryness.

Yield: 350 mg, quant. MW: 350.39, (C17H23FN4O3) MS: 351.6 (M+H)+, Method ESI+.

7-(4-{4-[(5S)-5-(Acetylamino-methyl)-2-oxo-oxazolidin-3-yl]-2-fluoro-phenylamino}-piperidin-1-yl)-1-cyclopropyl-6-fluoro-4-oxo-1,4-dihydro-[1,8]naphthyridine-3-carboxylic Acid A suspension of 100 mg N-{(5S)-3-[3-fluoro-4-(piperidin 4-ylamino)-phenyl]-2-oxo-oxazolidin-5-ylmethyl}acetamide (0.28 mmol), 80.66 mg 7-chloro-1-cyclopropyl-6-fluoro-1,4-dihydro-4-oxo-1,8-naphthyridine-3-carboxylic acid (0.28 mmol), 0.108 ml trimethylchlorosilane (0.84 mmol) and 0.16 ml triethylamine (1.12 mmol) in 2 ml DMSO was heated under stirring in a micro wave oven at 150° C. for 7 min: The DMSO was evaporated, the residue was purified by chromatography.

Yield: 54 mg, 31%. MW: 596.60, (C29H30F2N6O6) MS: 597.5 (M+H)+, Method ESI+.

Known building blocks:
3,4-difluorobenzene: 369-34-6, Aldrich 28-836-5
4-Amino-N-benzylpiperidine: 50541-93-0, Acros 18766
1,8-Naphthyridine-3-carboxylic acid, 7-chloro-1-cyclopropyl-6-fluoro-1,4-dihydro-4-oxo-(9CI): 100361-18-0, Louston International

Example 24

1-Cyclopropyl-6-fluoro-7-(4-{2-fluoro-4-[(5S)-5-(methoxythiocarbonylamino-methyl)-2-oxo-oxazolidin-3-yl]-phenyl}-piperazin-1-yl)-4-oxo-1,4-dihydro-[1,8]-naphthyridine-3-carboxylic Acid

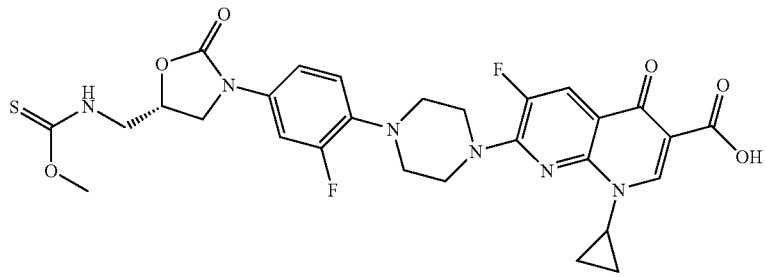

1-Cyclopropyl-6-fluoro-7-(4-{2-fluoro-4-[(5S)-5-(methoxy-thiocarbonylamino-methyl)-2-oxo-oxazolidin-3-yl]-phenyl}-piperazin-1-yl)-4-oxo-1,4-dihydro-[1,8]naphthyridine-3-carboxylic Acid A mixture of 100 mg {[(5S)-3-[3-fluoro-(1-piperazinyl)phenyl]-2-oxo-5-oxalidinyl]methyl}-carbamothioic acid methyl ester (0.27 mmol), 76.71 mg 7-chloro-1-cyclopropyl-6-fluoro-1,4-dihydro-4-oxo-1,8-naphthyridine-3-carboxylic acid (0.27 mmol), 68.65 µl trimethylchlorosilane (0.54 mmol) and 113.49 µl triethylamine (0.81 mmol) in 3 ml acetonitrile was stirred in micro wave for 8 min at 150° C. The reaction was diluted with water, and the precipitate was filtered and purified by chromatography using a dichloromethane/methanol 9/1 with 1% acetic acid.

Yield: 50 mg, 23%. MW: 614.63, (C28H28F2N6O6S) MS: 615.2 (M+H)+, 613.5 (M−H)−, Method ESI+, Method ESI−.

Known building blocks:

Carbamothioic acid, {[(5S)-3-[3-fluoro-(1-piperazinyl) phenyl]-2-oxo-5-oxalidinyl]methyl}-,o-methyl ester(9cl): 268208-73-7; WO 0027830

1,8-Naphthyridine-3-carboxylic acid, 7-chloro-1-cyclo-propyl-6-fluoro-1,4-dihydro-4-oxo-(9CI): CAS 100361-18-0, Louston International

Example 25

1-Cyclopropyl-6-fluoro-7-(4-{2-fluoro-4-((5)-5-(methylsulfanylthiocarbonylamino-methyl)-2-oxo-oxazolidin-3-yl]-phenyl}-piperazin-1-yl)-4-oxo-1,4dihydro-[1,8]naphthyridine-3-carboxylic Acid

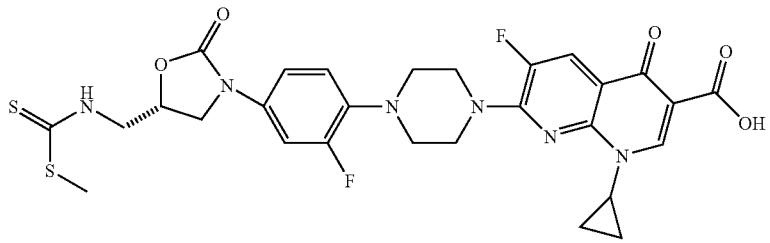

4-{2-Fluoro-4-[(5S)-5-(methylsulfanylthiocarbonylamino-methyl)-2-oxo-oxazolidin-3-yl]-phenyl}-piperazine-1-carboxylic Acid Tert-Butyl Ester A mixture of 500 mg 1-piperazinecarboxylic acid, 4-[4-[(5S)-5-[(acetylamino)methyl]2-oxo-3-oxazolidinyl]-2-fluoro-phenyl]-1,1-dimethylethyl ester, (1.26 mmol), 0.152 ml carbon disulfide (2.53 mmol) and 0.176 ml triethylamine (1.26 mmol) in 5 ml THF was stirred at 0° C. for 7 h. 79 µl methyliodide (1.26 mmol) was added dropwise to the reaction at 0° C., and the mixture was stirred at room temperature for 1 h. The mixture diluted with ethyl acetate and the org. layer was washed with water and brine, dried over Mg sulfate, filtered and the filtrate evaporated.

Yield: 510 mg, 83%. MW: 484.61, (C21H29FN4O4S2) MS: 485.0 (M+H)+)−, Method ESI+.

[(5S)-3-(3-Fluoro-4-piperazin-1-yl-phenyl)-2-oxo-oxazolidin-5-ylmethyl]-dithiocarbamic Acid Methyl Ester A suspension of 510 mg 4-{2-fluoro-4-[(5S)-5-(methylsulfanylthiocarbonylamino-methyl)2-oxo-oxazolidin-3-yl]-phenyl}-piperazine-1-carboxylic acid tert-butyl ester (1.05 mmol) in 1.25 M/methanol was stirred for 5 days. The solvent was evaporated and the residue digested in water. The water layer was neutralized at pH 7 with a saturated solution of sodium bicarbonate and evaporated to dryness. The residue was digested in CH2Cl2/MeOH. The salts were filtered and the solvent evaporated:

Yield: 250 mg, 25%. MW: 384.49, (C16H21FN4O2S2) MS: 385.5 (M+H)+, Method ESI+.

1-Cyclopropyl-6-fluoro-7-(4-{2-fluoro-4-((5S)-5-(methyl-sulfanylthiocarbonylamino-methyl)-2-oxo-oxazolidin-3-yl]-phenyl}-piperazin-1-yl)-4-oxo-1,4dihydro-[1,8]naphthyridine-3carboxylic Acid A mixture of 100 mg [(5S)-3-(3-fluoro-4-piperazin-1-yl-phenyl)-2-oxo-oxazolidin-5-ylmethyl]-dithiocarbamic acid methyl ester (0.26 mmol), 73.51 mg 7-chloro-1-cyclopropyl-6-fluoro-1,4-dihydro-4-oxo-1,8-naphthyridine-3-carboxylic acid (0.26 mmol) 108 µl triethylamine (0.78 mmol) and 65 µl trimethyl-chlorsilane (0.52 mmol), in acetonitrile was stirred in a micro wave oven for 8 min at 150° C. The solution was decanted from sticky solid, evaporated and the residue digested in water. The solid was filtered and the purified by chromatography using a 9/1 dichloromethane/methanol mixture with 1% acetic acid.

Yield: 50 mg 30%. MW: 630.70, (C28H28F2N6O5S2) MS: 631(M+H)+.

Known building blocks:
1-piperazinecarboxylic acid, 4-[4-[(5S)-5-[(acetylamino)-methyl]2-oxo-3-oxazolidinyl]-2-fluorophenyl]-,1,1-dimethylethyl ester, (S)-(9cl): 154990-65-5, U.S. Pat. No. 5,547,950
1,8-Naphthyridine-3-carboxylic acid, 7-chloro-1-cyclo-propyl-6-fluoro-1,4-dihydro-4-oxo-(9Cl): 100361-18-0, Louston International

Example 26

1-Cyclopropyl-6-fluoro-{4-[2-fluoro-4-{(5S)-2-oxo-5-thioureidomethyl-oxazolidin-3-yl}-phenyl]-piperazin-1-yl}-4-oxo-1,4-dihydro-[1,8]naphthyridine-3-carboxylic Acid

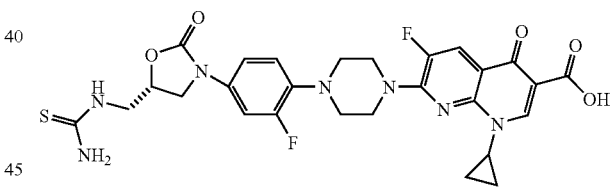

4-[2-Fluoro-4-{(5S)-2-oxo-5-thioureidomethyl-oxazolidin-3-yl}-phenyl]-piperazine-1-carboxylic Acid Tert-Butyl Ester A suspension of 1 g of 4-[2-fluoro-4-[(5R)-5-(isothiocyanatomethyl)-2-oxo-3-oxazolidinyl]phenyl])-1-piperazinecarboxylic acid tert-butyl ester (2.29 mmol) in 5 ml methanol and 5 ml ammoniac 2N in ethanol was stirred at 0° C. for 3 h. and at RT for 1 h. The precipitate was filtered and washed with ether.

Yield: 649 mg, 62%. MW: 453.53, (C20H28FN5O4S) MS: 454 (M+H)+, Method ESI+.

[(5S)-3-(3-Fluoro-4-piperazin-1-yl-phenyl)-2-oxo-oxazolidin-5-ylmethyl]-thiourea A solution of 649 mg 4-[2-fluoro-4-{(5S)-2-oxo-5-thioureidomethyl-oxazolidin-3-yl}-phenyl]-piperazine-1-carboxylic acid tert-butyl ester (1.43 mmol) in a mixture of 6 ml of a 1.25 M solution of hydrochloric acid in methanol and 1 drop water was stirred for 4 days. The solvent was evaporated, and the residue was neutralized at pH 7 with a saturated solution of sodium bicarbonate. The water was evaporated and the residue was digested in a 95/5 dichloromethane/methanol mixture and the solid filtered. The filtrate was purified by chromatography using a 95/5 dichloromethane/methanol mixture with 1% acetic acid.

Yield: 250 mg, 50%. MW: 353.42, (C15H20FN5O2S) MS: 354 (M+H)$^+$, Method ESI$^+$.

1-Cyclopropyl-6-fluoro-{4-[2-fluoro-4-{(5S)-2-oxo-5-thioureidomethyl-oxazolidin-3-yl}-phenyl]-piperazin-1-yl}-4-oxo-1,4-dihydro-[1,8]naphthyridine-3-carboxylic Acid A mixture of 100 mg [(5S)-3-(3-fluoro-4-piperazin-1-yl-phenyl)-2-oxo-oxazolidin-5-ylmethyl]-thiourea (0.28 mmol), 87.98 mg 7-chloro-1-cyclopropyl-6-fluoro-1,4-dihydro-4-oxo-1,8-naphthyridine-3-carboxylic acid (0.31 mmol), 71.57 µl trimethylchlorosilane (0.56 mmol) and 118.31 µl triethylamine (1.4 mmol) in acetonitrile was stirred in a micro wave oven for 8 min at 150° C. The reaction mixture was diluted with water and the solid filtered. The solid was purified by chromatography using a 95/5 dichloromethane/methanol mixture with 1% acetic acid as eluent to leave 50 mg of an oily residue which was crystallized from a ETOAC/hexane mixture.

Yield: 30 mg, 17%. MW: 599.62, (C27H27F2N7O5S) MS: 600 (M+H)$^+$, Method ESI$^+$.

Known building blocks:

1-piperazinecarboxylic acid, 4-[2-fluoro-4-[(5R)-5-(isothiocyanatomethyl)-2-oxo-3-oxazolidinyl]phenyl]-,1,1-dimethylester(9cl): WO 0027830

7-chloro-1-cyclopropyl-6-fluoro-1,4-dihydro-4-oxo-1,8-naphthyridine-3-carboxylic acid: 100361-18-0, Louston International Example 27

7-(4-{4-[5(S)-5-(Acetylamino-methyl)-2-oxo-oxazolidin-3-yl]-2-fluoro-phenoxy}-piperidin-1-yl)-1-cyclopropyl-6-fluoro-4-oxo-1,4-dihydro-[1,8]naphthyridine-3-carboxylic Acid A mixture of 7-chloro-1-cyclopropyl-6-fluoro-4-oxo-1,4-dihydro-[1,8]naphthyridine-3-carboxylate (80 mg), (S)—N-[[3-(3-fluoro-4-(4-piperidinyloxy)-phenyl]-2-oxo-5-oxazolidinyl]-methyl]acetamide (described in WO0146164; 100 mg), triethyl-amine (120 µL) and trimethylchlorsilane (72 µL) in DMSO (2 mL) were stirred at 150° C. for 5 minutes (microwave). The solvent was evaporated and the crude reaction was taken up with water. The resulting solid was filtered and chromatographed over silica gel (dichloromethane/methanol 95:5). The interesting fractions were collected and recrystallised from ethyl acetate/n hexane affording 70 mg (41%) of colorless material.

$C_{29}H_{29}F_2N_5O_7$ (597.58)
MS: 598.5 (M+H); 596.4 (M−H).

Example 28

7-(4-{4-[5(S)-5-(Acetylamino-methyl)-2-oxo-oxazolidin-3-yl]-2-fluoro-phenoxy}-piperidin-1-yl)-1-cyclopropyl-6-fluoro-4-oxo-1,4-dihydro-quinoline-3-carboxylic Acid A mixture of 7-chloro-1-cyclopropyl-6-fluoro-4-oxo-1,4-dihydro-quinoline-3-carboxylate boron diacetate (described in WO8807998; 175 mg, 0.42 mmol (S)—N-[[3-(3-fluoro-4-(4-piperidinyloxy)-phenyl]-2-oxo-5-oxazolidinyl]methyl] acetamide (150 mg, 0.42 mmol) and DABCO (47 mg, 0.42 mmol) were stirred at 150° C. in 2 ml DMSO for 7-minutes (microwave). The solvent was evaporated and the crude reaction was taken up with water. The resulting solid was filtered and chromatographed over silica gel (dichloromethane/methanol 95:5). The interesting fractions were collected and crystallised from acetonitrile affording 23 mg (9%) of colorless material.

$C_{30}H_{30}F_2N_4O_7$ (596.59)
MS: 597.5 (M+H).

Example 29

7-(4-{4-[5(S)-5-(Acetylamino-methyl)-2-oxo-oxazolidin-3-yl]-2-fluoro-phenylsulfanyl}-piperidin-1-yl)-1-cyclopropyl-6-fluoro-4-oxo-1,4-dihydro-quinoline-3-carboxylic Acid Was prepared in analogy to example 28 starting from 7-chloro-1-cyclopropyl-6-fluoro-4-oxo-1,4-dihydro-quinoline-3-carboxylate boron diacetate and (S)—N-[[3-(3-fluoro-4-(4-piperidinylsulfanyl)-phenyl]-2-oxo-5-oxazolidinyl]methyl]-acetamide. The later being obtained from 4-mercapto-piperidine-1-carboxylic acid tert-butyl ester (J. Antibiotics, 1995, 48, 408-16).

$C_{30}H_{30}F_2N_4O_{6S}$ (612.66)
MS: 613.8 (M+H)$^+$.

Example 30

7-(4-{4-[5(S)-5(Acetylamino-methyl)-2-oxo-oxazolidin-3-yl]-2-fluoro-phenylsulfanyl}-piperidin-1-yl)-1-cyclopropyl-6-fluoro-4-oxo-1,4-dihydro-[1,8]naphthyridine-3-carboxylic Acid Was prepared in analogy to example 27 starting from 7-chloro-1-cyclopropyl-6-fluoro-4-oxo-1,4-dihydro-[1,8]naphthyridine-3-carboxylate and (S)—N-[[3-(3-fluoro-4-(4-piperidinylsulfanyl)-phenyl]-2-oxo-5-oxazolidinyl]methyl] acetamide.

$C_{29}H_{29}F_2N_5O_{6S}$ (612.66)
MS: 613.8 (M+H).

All examples were tested against several gram positive and gram negative bacteria. They all have a broader and more pronounced activity than the corresponding quinolone and oxazolidinone as well as a 1+1 combination of these two compounds.

Typical MIC range (mg/l)

S. aureus (MRSA): 0.125-2 (linezolid 1-2, ciprofloxacin: 0.5-32)

S. aureus (MSSA): 0.06-1 (linezolid: 1-2, ciprofloxacin: 0.125-1)

E. faecalis=<0.03-1 (linezolid: 0.5-2, ciprofloxacin: 0.5-32)

E. faecium=<0.03-1 (linezolid: 1-2, ciprofloxacin: 0.25-32)

S. pneumoniae=<0.03-1 (linezolid: 0.125-1), ciprofloxacin: 1-4)

To summarize, the compounds, pharmaceutical compositions and products of the present invention can be used as antimicrobial, especially antibacterial agents.

The invention claimed is:

1. Compounds of Formula (I):

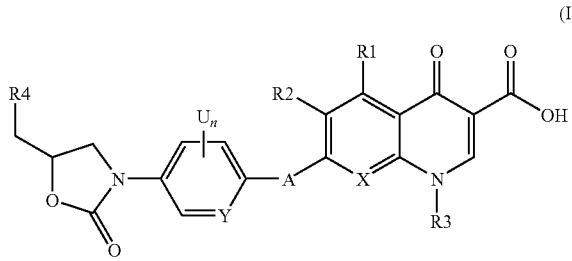

wherein,
(a) A is a group of the formula —V—W—,
V being a group of the formula O, S, SO, or $SO_2$,
W being a heterocycloalkyl group with 4 to 7 ring atoms or a alkylheterocycloalkyl group with 4 to 7 ring atoms and 1 to 4 carbon atoms in the alkyl chain, heteroatoms of the heterocycloalkyl group or the alkylheterocycloalkyl group consisting of 1 N,
W being optionally substituted by at least one substituent selected from the group consisting of F, Cl, Br, OH, $NH_2$, SH, $N_3$, $NO_2$, an alkyl group, and a heteroalkyl group;
(b) X is CR5;
(c) Y is CR6 or N;
(d) U is F or Cl;
(e) n is 0 or 1;
(f) R1 is H, F, Cl, Br, I, OH, $NH_2$, an alkyl group or a heteroalkyl group;
(g) R2 is H, F or Cl;
(h) R3 is an ethyl, a 2-propyl, a C3-C6 cycloalkyl, a phenyl or a pyridyl group wherein all these groups may be substituted by one, two or more fluorine atoms or amino groups;
(i) R4 is a group of the formula —NHCOCH=CHAryl, —O-Hetero-aryl, —$NHSO_2Me$, —NHCOOMe, —$NHCS_2Me$, —$NHCSNH_2$, —NHCSOMe or —NHCOMe;
(j) R5 is H, F, Cl, OH, $NH_2$, an alkyl group or a heteroalkyl group, or
(k) R3 and R5 together form a bridge of the formula —O—$CH_2$—N(Me)- or —O—$CH_2$—CH(Me)-; and
(l) R6 is H, F, Cl or OMe;
or a pharmacologically acceptable salt, hydrate or formulation thereof.

2. Compounds according to claim 1, wherein R1 is H or $NH_2$.

3. Compounds according to claim 1, wherein R2 is H or F.

4. Compounds according to claim 1, wherein R3 is a cyclopropyl group.

5. Compounds according to claim 1, wherein R4 is an acetylamino group.

6. Compounds according to claim 1, wherein R5 is H, F, Cl or a methoxy group which may be substituted by up to three fluorine atoms or a $CF_3$ group.

7. Compounds according to claim 1, wherein X is CH.

8. Compounds according to claim 1, wherein Y is N or CF.

9. Compounds according to claim 1, wherein n is 0.

10. Compounds according to any one of claims 1 to 9 wherein A is a group of the formula —V—W—, wherein V is a group of the formula O, S, SO, $SO_2$, $SO_2NH$, $PO_4$, —NH—CO—NH—, —CO—NH—, —CO—, —$CH_2$—, —CO—O—, —$(CH_2)_{1-3}$—O—, —CH=CH—C(O)—, or —NH—CO—O— and W is a heterocycloalkyl group with 4 to 7 ring atoms or a alkylheterocycloalkyl group with 4 to 7 ring atoms and 1 to 4 carbon atoms in the alkyl chain; all these groups may be substituted by 1, 2, 3 or 4 fluorine atoms, methyl or methoxy groups.

11. Compounds according to any one of claims 1 to 9 wherein A is a group of the formula

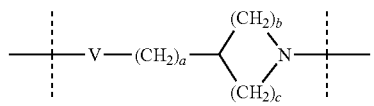

wherein
V is a group of the formula O, S, SO, $SO_2$, $SO_2NH$, $PO_4$, —NH—CO—NH—, —CO—NH—, —CO—, —$CH_2$—, —CO—O—, —$(CH_2)_{1-3}$—O—, —CH=CH—C(O)—, or —NH—CO—O—;
a is 0, 1, 2, 3 or 4;
b is 0, 1, 2, 3 or 4;
c is 0, 1, 2, 3 or 4 and
1, 2, 3 or 4 hydrogen atoms may be substituted by F, a methyl- or a methoxy group.

12. Compounds according to claim 10 or 11 wherein V is O, S, SO or $SO_2$.

13. Compounds according to claim 11 wherein V is O; a is 0 or 1; b is 1 or 2 and c is 1 or 2.

14. Compounds according to any one of claims 1 to 12 wherein A is a group of the formula

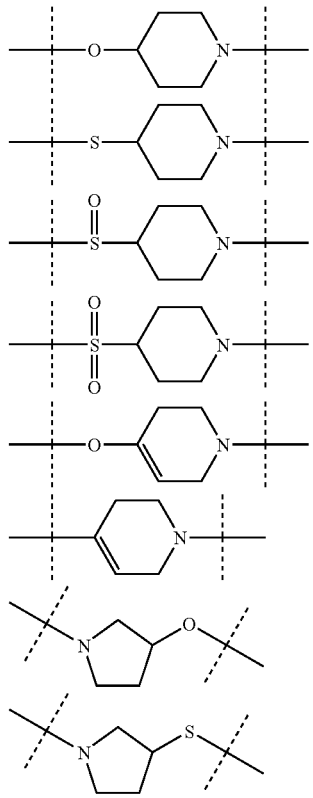

-continued

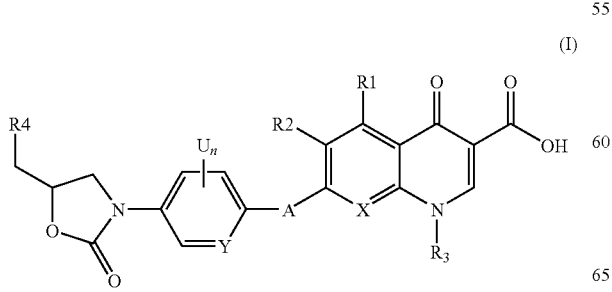

wherein 1, 2, 3 or 4 hydrogen atoms may be substituted by F, a methyl- or a methoxy group.

15. Compounds according to claim 1, wherein the absolute configuration at C-5 of the oxazolidinone ring is (S) according to the Cahn-Ingold-Prelog nomenclature system.

16. Pharmaceutical compositions containing a compound according to claim 1 and optionally carriers and/or adjuvants and/or diluents.

17. A compound of Formula (I):

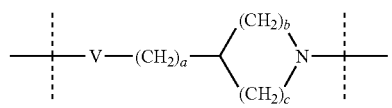

wherein,
(a) A is a group of the formula —V—W—,
V being a group of the formula O, S, SO, or $SO_2$,
W being a heterocycloalkyl group with 4 to 7 ring atoms or a alkylheterocycloalkyl group with 4 to 7 ring atoms and 1 to 4 carbon atoms in the alkyl chain, heteroatoms of the heterocycloalkyl group or the alkylheterocycloalkyl group consisting of 1 N;
(b) X is CR5;
(c) Y is CR6 or N;
(d) U is F or Cl;
(e) n is 0 or 1;
(f) R1 is H, F, Cl, Br, I, OH, $NH_2$, an alkyl group or a heteroalkyl group;
(g) R2 is H, F or Cl;
(h) R3 is an ethyl, a 2-propyl, a C3-C6 cycloalkyl, a phenyl or a pyridyl group wherein all these groups may be substituted by one, two or more fluorine atoms or amino groups;
(i) R4 is a group of the formula —NHCOCH=CHAryl, —O-Hetero-aryl, —$NHSO_2Me$, —NHCOOMe, —$NHCS_2Me$, —$NHCSNH_2$, —NHCSOMe or —NHCOMe;
(j) R5 is H, F, Cl, OH, $NH_2$, an alkyl group or a heteroalkyl group, or
(k) R3 and R5 together form a bridge of the formula —O—$CH_2$—N(Me)- or —O—$CH_2$—CH(Me)-; and
(l) R6 is H, F, Cl or OMe;
or a pharmacologically acceptable salt, hydrate or formulation thereof.

18. Compounds according to claim 1, wherein W is optionally substituted by at least one substituent selected from the group consisting of F, Cl, Br, OH, $NH_2$, SH, $N_3$, $NO_2$, an alkyl selected from the group consisting of methyl or ethyl, and a heteroalkyl selected from the group consisting of methoxy, methylamino, dimethylamino, and cyanide.

19. Compounds according to claim 1, wherein W is a heterocycloalkyl group selected from the group consisting of a azepanyl, piperinyl, pyrrolidinyl and azetidinyl.

20. Compounds according to claim 17, wherein W is a heterocycloalkyl group selected from the group consisting of a azepanyl, piperinyl, pyrrolidinyl and azetidinyl.

21. Compounds according to claim 1 wherein W is optionally substituted by 1, 2, 3 or 4 fluorine atoms, methyl or methoxy groups.

22. Compounds according to claim 1, wherein A is a group of the formula $$-\!\!-\!\!V\!\!-\!\!(CH_2)_a\!\!-\!\!\!\begin{array}{c}(CH_2)_b\\ \diagdown\\ \diagup\\ (CH_2)_c\end{array}\!\!\!N\!\!-\!\!\!-$$

wherein
V is a group of the formula O, S, SO, or $SO_2$;
a is 0, 1, 2, 3 or 4;
b is 0, 1, 2, 3 or 4; and
c is 0, 1, 2, 3 or 4 and
1, 2, 3 or 4 hydrogen atoms are optionally substituted by F, a methyl, a methoxy, or a hydroxy group.

23. Compounds according to claim 22, wherein V is O, S, SO or $SO_2$.

24. Compounds according to claim 11 wherein V is O; a is 0 or 1; b is 1 or 2 and c is 1 or 2.

25. Compounds according to claim 11 wherein A is a group of the formula
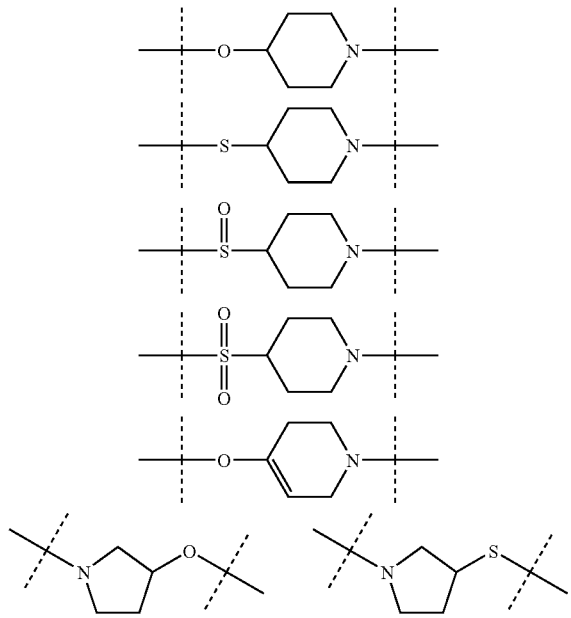
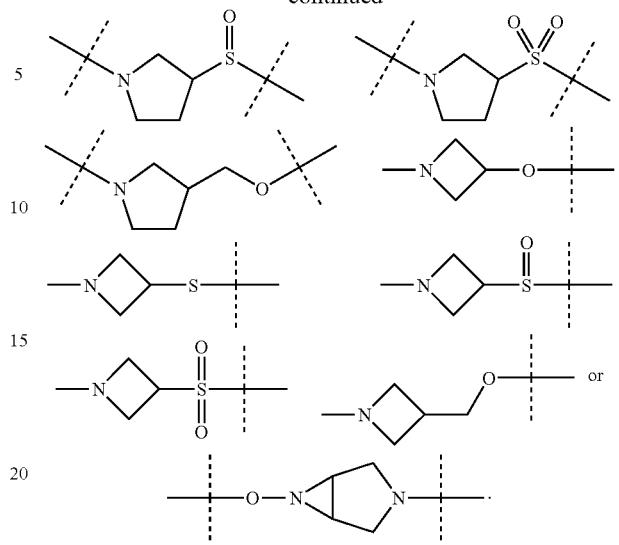
26. Pharmaceutical compositions containing a compound according to claim 17 and optionally carriers and/or adjuvants and/or diluents.
* * * * *